United States Patent
Hernando et al.

(10) Patent No.: US 8,252,760 B2
(45) Date of Patent: Aug. 28, 2012

(54) COMPOSITIONS AND METHODS FOR DIAGNOSING AND TREATING MELANOMA

(75) Inventors: Eva Hernando, New York, NY (US); Miguel F. Segura, New York, NY (US); Douglas Hanniford, New York, NY (US); Silvia Menendez, New York, NY (US)

(73) Assignee: New York University, New York, NY (US)

( * ) Notice: Subject to any disclaimer, the term of this patent is extended or adjusted under 35 U.S.C. 154(b) by 173 days.

(21) Appl. No.: 12/410,348

(22) Filed: Mar. 24, 2009

(65) Prior Publication Data

US 2009/0238896 A1    Sep. 24, 2009

Related U.S. Application Data

(60) Provisional application No. 61/038,990, filed on Mar. 24, 2008.

(51) Int. Cl.
- *A61K 31/70* (2006.01)
- *C07H 21/02* (2006.01)
- *C07H 21/04* (2006.01)

(52) U.S. Cl. ............ 514/44 A; 536/24.1; 536/24.5
(58) Field of Classification Search ........... 514/44; 536/23.5, 24.5
See application file for complete search history.

(56) References Cited

U.S. PATENT DOCUMENTS 7,683,036 B2 *  3/2010  Esau et al. ............ 514/44 R

FOREIGN PATENT DOCUMENTS

WO    WO2006/137941    12/2006

OTHER PUBLICATIONS

Segura et al. (Proceedings of the National Academy of Sciences, 2009 vol. 106, No. 6:1814-1819).*
Bemis, T. L., et al., MicroRNA-137 Targets Microphthalmia-Associated Transcription Factor in Melanoma Cell Lines, Cancer Res (2008), 68:1362-1368.
Blower, E. P., et al., MicroRNA expression profiles for the NCI-60 cancer cell panel, Mol Cancer Ther (2007), 6:1483-1491.
Calin, G. A., Croce, C. M., MicroRNA signatures in human cancers, Nat Rev Cancer (2006), 6: 857-866.
Calin, G. A., et al., A MicroRNA signature associated with prognosis and progression in chronic lymphocytic leukemia, N Engl. Journal Med. (2005), 353:1793-1801.
Cimmino, A., et al., miR-15 and miR-16 induce apoptosis by targeting BCL2, Proc Natl Acad Sci U S A (2005), 102:13944-13949.
Croce, C. M., Calin, G. A., miRNAs, cancer, and stem cell division, Cell (2005), 122:6-7.
Felicetti, F., et al., The Promyelocytic Leukemia Zinc Finger-MicroRNA-221/-222 Pathway Controls Melanoma Progression through Multiple Oncogenic Mechanisms, Cancer Res (2008), 68:2745-2754.

(Continued)

*Primary Examiner* — Terra Cotta Gibbs
(74) *Attorney, Agent, or Firm* — Fish & Richardson P.C.

(57) ABSTRACT

Described herein are compositions and methods for the diagnosis, prognosis, prevention and treatment of melanoma or melanoma associated symptoms. The compositions are microRNA molecules associated with melanoma, as well as various nucleic acid molecules relating thereto or derived therefrom.

10 Claims, 14 Drawing Sheets

OTHER PUBLICATIONS

Glud, M., et al., MicroRNA expression in melanocytic nevi: the usefulness of formalin-fixed, paraffin-embedded material for miRNA microarray profiling, Journal of Investigative Dermatology advance online publication (2008), 1-6.

Guo, Y., et al., Distinctive microRNA profiles relating to patient survival in esophageal squamous cell carcinoma, Cancer Res (2008), 68:26-33.

Hayashita, Y., et al., A polycistronic microRNA cluster, miR-17-92, is overexpressed in human lung cancers and enhances cell proliferation, Cancer Res (2005), 65:9628-9632.

He L., et al., A microRNA polycistron as a potential human oncogene, Nature (2005), 435:828-833.

Hebert, C., High mobility group A2 is a target for miRNA-98 in head and neck squamous cell carcinoma, Mol Cancer (2007), 6:5.

Hernando E., microRNAs and cancer: role in tumorigenesis, patient classification and therapy, Clin Transl Oncol (2007), 9(3):155-60.

Igoucheva, O., Alexeev, V., MicroRNA-dependent regulation of cKit in cutaneous melanoma, Biochemical and Biophysical Reserach Communications (2009), 379:790-794.

Johnson, S. M., et al., RAS is regulated by the let-7 microRNA family, Cell (2005), 120:635-647.

Landgraf, P., et al., A mammalian microRNA expression atlas based on small RNA library sequencing, Cell (2007), 129:1401-1414.

Lee, Y. S., Dutta, A. The tumor suppressor microRNA let-7 represses the HMGA2 oncogene. Genes Dev (2007), 21:1025-1030.

Lodygin, D., et al., Inactivation of miR-34a by aberrant CpG methylation in multiple types of cancer, Cell Cycle (2008), 7:16, 2591-2600.

Lu, J., et al., MicroRNA expression profiles classify human cancers, Nature (2005) 435:834-838.

Ma, L., et al., Tumour invasion and metastasis initiated by microRNA-10b in breast cancer, Nature (2007), 449:682-688.

Mayr, C., et al., Disrupting the pairing between let-7 and Hmga2 enhances oncogenic transformation, Science (2007), 315:1576-1579.

Migliore, C. et al., MicroRNAs Impair MET-Mediated Invasive Growth, Cancer Res (2008), 68:10128-10136.

Muller, D.W., Bosserhoff, A., Integrin β-expression is regulated by let-7a miRNA in malignant melanoma, Institute of pathology, Oncogene (2008), 27:6698-6706.

Mueller, D.W., et al., miRNA Expression Profiling in Melanocytes and Melanoma Cell Lines Reveals miRNAs Associated with Formation and Progression of Malignant Melanoma, J Invest Dermatol. (2009) Feb 12. [Epub ahead of print].

Ozsolak, F., et al., Chromatin structure analyses identify miRNA promoters, Genes Dev. (2008), 22:3172-3183.

Sand, M., et al., MicroRNAs and the skin: Tiny players in the body's largest organ, Journal of Dermatological Science (2008), 53:169-175.

Schultz, J., et al., MicroRNA let-7b targets important cell cycle molecules in malignant melanoma cells and interferes with anchorage-independent growth, Cell Research (2008), 18:549-557.

Segura M.F., et al., Aberrant miR-182 expression promotes melanoma metastasis by repressing FOXO3 and microphthalmia-associated transcription factor, Proc Natl Acad Sci USA (2009), 106(6):1814-9.

Takamizawa, J., et al. Reduced expression of the let-7 microRNAs in human lung cancers in association with shortened postoperative survival, Cancer Res (2004), 64:3753-3756.

Tavazoie, S. F., et al., Endogenous human microRNAs that suppress breast cancer metastasis, Nature (2008), 451:147-152.

Voorhoeve, P. M., et al., A genetic screen implicates miRNA-372 and miRNA-373 as oncogenes in testicular germ cell tumors, Cell (2006), 124:1169-1181.

Worley, L., et al., Micro-RNAs associated with metastasis in uveal melanoma identified by multiplexed microarray profiling, Melanoma Research (2008), 18:184-190. Cancer Res 68, 1362-1368.

Xu, S., et al., MicroRNA (miRNA) transcriptome of mouse retina and identification of a sensory organ-specific miRNA cluster, J. Biol Chem (2007), 282:25053-25066.

Yanaihara, N., et al., Unique microRNA molecular profiles in lung cancer diagnosis and prognosis, Cancer Cell (2006), 9:189-198.

Yu, S. L., et al., MicroRNA Signature Predicts Survival and Relapse in Lung Cancer, Cancer Cell (2008), 13:48-57.

Molnar, et al, 2008. "Changes in miRNA expression in solid tumors: An miRNA profiling in melanomas." Seminars in Cancer Biology 18: 111-122.

Bandres, et al, 2006. "Identification by Real-Time PCR of 13 mature microRNAs differentially expressed in colorectal cancer and non-tumoral tissues." Molecular Cancer vol. 5, Article 29. 10 pages.

Navarro, et al, 2008. "MicroRNA expression profiling in classic Hodgkin lymphoma." Blood 111(5): 2825-2832.

Gaur, et al, 2007. "Characterization of MicroRNA Expression Levels and Their Biological Correlates in Human Cancer Cell Lines." Cancer REs. 67(6): 2456-2468.

Zhang, Lin et al. "microRNAs exhibit high frequency genomic alterations in human cancer," Proceedings of the National Academy of Sciences, vol. 103, No. 24, Jun. 13, 2006, pp. 9136-9141.

Segura, Miguel F. et al. "Aberrant miR-182 expression promotes melanoma metastasis by repressing F0X03 and microphthalmia-associated transcription factor," (Article and Supporting Information) Proceedings of the National Academy of Sciences of the United States of America, Feb. 10, 2009, vol. 106, No. 24, pp. 1814-1810, and Supporting Information, pp. 1-10.

Huynh, C. et al. "Efficient in vivo microRNA targeting of liver metastasis," Oncogene, vol. 30. No. 12, Mar. 24, 2011, pp. 1481-1488.

Vermeulen, Annaleen, et al. "Double-stranded regions are essential design components of potent inhibitors of RISC function," RNA (Cold Spring Harbor) vol. 13, No. 5, May 2007, pp. 723-730.

European Patent Office Extended Search Report dated Oct. 6, 2011 in co-pending Application No. 09723968.5, 9 pages.

* cited by examiner

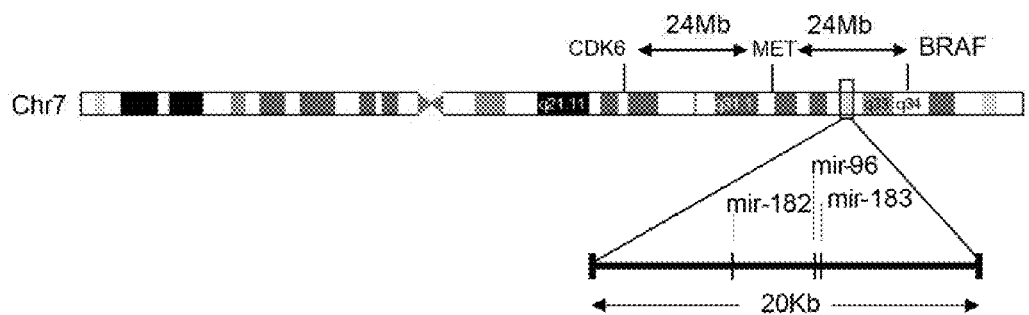

FIG. 5A

```
hsa-mir-182    UUUGGCAAUGGUAGAACUCACACU
hsa-mir-183    UAUGGCACUGGUAGAAUUCACU--
hsa-mir-96     UUUGGCACUAGCACAUUUUUGCU-
               * ***** * * * *   *
```

FIG. 5B

```
hsa-mir-96    ------------------UGGCCGAUUU-UGGCACUAGCACAUUUUUGCUUG-UGUCUCUC
hsa-mir-183   CCGCAGAGUGUGACUCCUGUUCUGUGUAUGGCACUGGUAGAAUUCACGUG-AACAGUCU
hsa-mir-182   ----GAGCUGCUUGCCUCCCCCGUUUUUGGCAAUGGUAGAACUCACACUGGUGAGGUAA
                  * * ***** * * *  *     ** hsa-mir-96    CGCUCUGAGCAAUCAUGUGCAGUGCCA-AUAUGGGAAA-----------------
hsa-mir-183   CAGUCAGUG-AAUUAC-CGAAGGGCCAUAAACAGAGCAGAGACAGAUCCACGA-
hsa-mir-182   CAGGAUCCGGUGGUUCUAGACUUGCCAACUAUGGGGCGAGGACUCAGCCGGCAC
              *        *       * ****  *  *
```

FIG. 5C

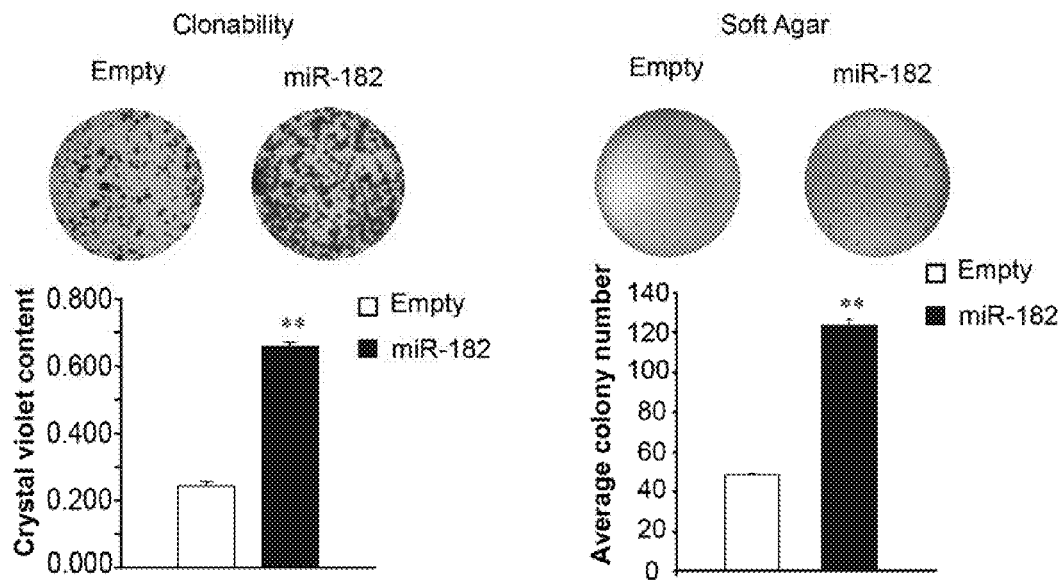
FIG. 7A
FIG. 7B
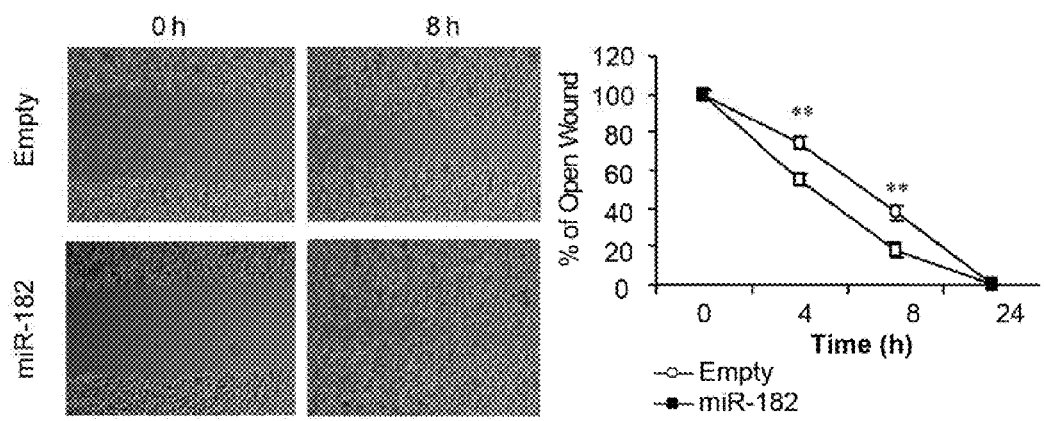
FIG. 7C

COMPOSITIONS AND METHODS FOR DIAGNOSING AND TREATING MELANOMA

CROSS REFERENCE TO RELATED APPLICATIONS

The present application claims the benefit of U.S. Provisional Application Ser. No. 61/038,990, filed on Mar. 24, 2008, the contents of which are hereby incorporated by reference in its entirety.

FIELD OF THE INVENTION

The invention relates to compositions and methods for the diagnosis, prevention and treatment of melanoma or melanoma associated symptoms. Specifically the invention relates to microRNA molecules associated with melanoma, as well as various nucleic acid molecules relating thereto or derived therefrom.

BACKGROUND OF THE INVENTION microRNAs (miRNAs, miRs) are endogenous non-coding small RNAs that interfere with the translation of coding messenger RNAs (mRNAs) in a sequence specific manner (Meister et al., 2004), playing a critical role in the control of gene expression during development and tissue homeostasis (Chen et al., 2004; He and Hannon, 2004; Yi et al., 2006). Certain miRNAs have been shown to be deregulated in human cancer (Croce and Calin, 2005), and their specific over- or under-expression has been shown to correlate with particular tumor types (Calin and Croce, 2006; Lu et al., 2005), as well as to predict patient outcome (Calin et al., 2005; Guo et al., 2008; Takamizawa et al., 2004; Yanaihara et al., 2006; Yu et al., 2008). In some cases miRNA overexpression results in reduced expression of tumor suppressor genes (Hayashita et al., 2005; He et al., 2005; Voorhoeve et al., 2006), while loss of miRNA expression often leads to oncogene activation (Calin et al., 2005; Cimmino et al., 2005; Hebert et al., 2007; Johnson et al., 2005; Lee and Dutta, 2007; Mayr et al., 2007). Recent work has shown an essential role for miRNA deregulation in breast cancer metastasis (Ma et al., 2007; Tavazoie et al., 2008).

Malignant melanoma (MM) is one of the fastest growing malignancies in the United States (Benjamin et al., 2007), and its associated mortality continues to rise throughout the world (Geller et al., 2007). In addition to well defined genetic lesions (reviewed in Chin et al., 2006), melanomas are characterized by frequent chromosomal aberrations associated with tumor progression (Jonsson et al., 2007). In particular, melanomas display a characteristic pattern of genomic alterations involving miRNA genes.

However, there is an unmet need for new compositions and methods for diagnosis, prevention and treatment of melanoma or melanoma associated symptoms.

SUMMARY OF THE INVENTION

The present invention is based on the discovery that an exogenous expression of miR-182 (SEQ ID NO: 1) enhances the oncogenic behavior of melanoma cells in vitro and their metastatic potential in vivo, while its down-regulation blocks cell migration and triggers apoptosis. Furthermore, miR-182 regulates the levels of forkhead box O3 transcription factor (FOXO3) and M isoform of Microphthalmia-associated Transcription Factor (MITF-M).

Provided herein are methods for treating melanoma comprising administering to a subject in need thereof an effective amount of a composition comprising an isolated nucleic acid comprising a nucleic acid sequence that is complementary to a sequence selected from SEQ ID NO: 1, 5, 7, 8, 12, 14, or to a sequence at least about 80% identical thereto.

In one embodiment, the nucleic acid is a modified oligonucleotide. In a specific embodiment, such modified oligonucleotide has no more than one or two mismatches to said nucleic acid sequence. In certain embodiments, the modified oligonucleotide is administered at a dose within the range of 10-70 mg/Kg. The modified oligonucleotide can be administered one per day, once per week, once per two weeks, once per three weeks, or once per four weeks.

In another embodiment, the nucleic acid is a vector comprising said nucleic acid sequence.

In certain embodiments, the subject is a human.

In certain embodiments, administration of a composition of the invention comprises intravenous administration, intraperitoneal administration, subcutaneous administration, intratumoral administration, or chemoembolization.

In certain embodiments, the methods of the present invention further comprise administering at least one additional therapy. The additional therapy can be a chemotherapeutic agent. The chemotherapeutic agent can be selected from dacarbazine (DTIC), hydroxylurea, temozolomide, cisplatin, carboplatin, camptothecins, doxorubicin, cyclophosphamide, etoposide, vinblastine, Actinomycin D and cloposide. The additional therapy can be administered at the same time, less frequently, or more frequently than the composition of the invention.

In certain embodiments, the methods of treatment according to the invention are used to reduce the melanoma tumor size and/or melanoma tumor number and/or to prevent, or slow down melanoma recurrence and/or melanoma metastatic progression and, as a result, to extend the overall survival time of the subject.

The invention also provides a method of modulating the expression level of FOXO3, which method comprises introducing to a subject in need thereof an effective amount of a composition comprising a nucleic acid sequence selected from the group consisting of (a) SEQ ID NOS: 1, 5, 7, 8, 12, 14, and (b) sequences at least about 80% identical to (a).

In a more general aspect, the invention provides a method for modulating the expression level of a first nucleic acid, said method comprising introducing a second nucleic acid to the first nucleic acid, wherein the second nucleic acid is selected from the group consisting of (a) SEQ ID NOS: 1, 5, 7, 8, 12, 14, and (b) sequences at least about 80% identical to (a), wherein the second nucleic acid modulates the expression of the first nucleic acid. The first nucleic acid can be a target sequence of a miRNA, such as, e.g., a nucleic acid sequence comprising SEQ ID NO: 21. The second nucleic acid can be a miRNA, anti-miRNA or siRNA.

The invention further provides a method for diagnosis of melanoma in a subject, which method comprises (a) providing a biological sample from the subject; (b) obtaining an expression profile of a nucleic acid sequence selected from the group consisting of SEQ ID NOS: 1-14 and sequences at least about 80% identical thereto from said sample; and (c) comparing said obtained expression profile to a reference expression profile; wherein a differential expression of the nucleic acid in the subject as compared to the reference expression profile is diagnostic of the subject having melanoma.

The biological sample can be selected from the group consisting of bodily fluid, a cell line and a tissue sample. The tissue can be selected from fresh, frozen, fixed, wax-embedded or formalin fixed paraffin-embedded (FFPE) tissue. The tissue can be a skin tissue.

A kit for diagnosing a subject with melanoma is also provided. In a specific embodiment, the kit comprises a probe comprising a nucleic acid sequence that is complementary to a sequence selected from SEQ ID NO: 1-14; or to a sequence at least about 80% identical thereto.

These and other embodiments of the present invention will become apparent in conjunction with the figures, description and claims that follow.

BRIEF DESCRIPTION OF THE DRAWINGS

FIG. 7 demonstrates hsa-miR-182 ectopic expression potentiates the in vitro oncogenic behavior of murine B16F10 melanoma cells. (A), Colony formation assay on murine B16F10 melanoma cells transduced with empty vector (Empty) or with hsa-miR-182-expressing vector (miR-182). Graph is representative of three independent experiments (n=4). (B), Growth in soft agar (n=4) and (C) wound-healing assay (n=12) on B16F10 stably infected with empty vector (Empty) or hsa-miR-182 (miR182).

DETAILED DESCRIPTION

Figure 1A:
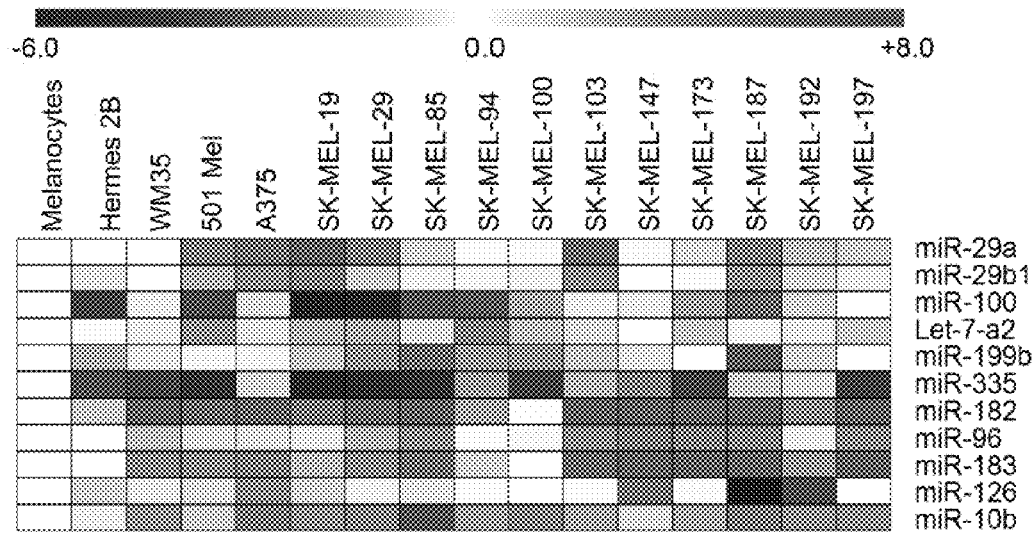
FIG. 1 shows that miR-182 is commonly overexpressed in human melanoma cell lines and tumors. (A) Heat map of expression of specific miRNAs (including SEQ ID NOS: 1-8) in human melanoma cell lines, assessed by real-time quantitative PCR (qRT-PCR). A shading scale (−5.5 to +8) depicts miRNA expression levels normalized to adult melanocytes. (B) Graph representing the expression of miR-182 (SEQ ID NO:1) (measured by miR-182 in situ hybridization (ISH) on melanoma tissue microarrays (TMAs)) in nevi, primary and metastatic melanoma human samples relative to the U6 control. The line indicates the mean value for each group (n is the number of clinical specimens). (C) Representative pictures of miR-182 expression in melanoma tissues at distinct disease stages (middle panels); U6 staining confirming the preservation of intact small RNAs on the same cases (left panels); Hematoxylin and eosin (H&E)-stained sections allowed the identification of tumor cells on each core (right). Arrowheads point to melanocyte nest (nevus). Bar=50 μm.

According to the present invention the expression of candidate miRNAs was validated in a subset of 3 samples of primary melanocytes and 11 metastatic melanoma cell lines. The data revealed few miRNAs (SEQ ID NOS: 1, 5, 8) that were consistently altered. Most of them were located in the long arm of chromosome 7, more precisely in the 7q32.1-q34 loci, which is frequently altered in melanoma and contains the BRAF oncogene. Selected miRNAs were transduced into primary melanocytes and in metastatic melanoma cell lines by using retroviral vectors. Changes in oncogenic properties have been observed revealing a critical role for microRNAs in melanoma genesis and progression. As a consequence of these results, cellular pathways governed by miR-182 become potential prognostic markers and molecular targets. Furthermore, it was demonstrated that miR-182 expression confers a survival advantage to melanoma cells, while its down-regulation blocks migration and triggers apoptosis. These results provide a rationale for miRNA silencing as a novel therapeutic strategy against human melanoma.

Methods and compositions are provided for the diagnosis, prognosis, prevention and treatment of melanoma. Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

1. DEFINITIONS a. Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

b. Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

c. Biological Sample

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

d. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

e. Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

f. Duration

"Duration" means the period of time during which an activity or event continues. In certain embodiments, the duration of treatment is the period of time during which doses of a pharmaceutical agent or pharmaceutical composition are administered.

g. Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

h. Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

i. Host Cell

"Host cell" used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

j. Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

k. Inhibit

"Inhibit" as used herein may mean prevent, suppress, repress, reduce or eliminate.

l. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

m. Mismatch

"Mismatch" means a nucleobase of a first nucleic acid that is not capable of pairing with a nucleobase at a corresponding position of a second nucleic acid.

n. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

o. Operably Linked

"Operably linked" used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

p. Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

q. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

r. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

s. Substantially Complementary

"Substantially complementary" used herein may mean that a first sequence is at least 60%-99% identical to the complement of a second sequence over a region of 8-50 or more nucleotides, or that the two sequences hybridize under stringent hybridization conditions.

t. Substantially Identical

"Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

u. Subject

As used herein, the term "subject" refers to a mammal, including both human and other mammals. The methods of the present invention are preferably applied to human subjects.

v. Therapeutically Effective Amount

As used herein the term "therapeutically effective amount" or "therapeutically efficient" as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

w. Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

x. Unit Dosage Form

"Unit dosage form," used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

y. Variant

"Variant" used herein to refer to a nucleic acid may mean (i) a portion of a referenced nucleotide sequence; (ii) the complement of a referenced nucleotide sequence or portion thereof, (iii) a nucleic acid that is substantially identical to a referenced nucleic acid or the complement thereof, or (iv) a nucleic acid that hybridizes under stringent conditions to the referenced nucleic acid, complement thereof, or a sequences substantially identical thereto.

z. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

aa. About

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to +10%, more preferably up to ±5%, and more preferably still up to ±1% of a given value. Alternatively, the term can mean within an order of magnitude, preferably within 2-fold, of a value. Where particular values are described in the application and claims, unless otherwise stated, the term "about" is implicit and in this context means within an acceptable error range for the particular value.

2. MICRORNA

A gene coding for a miRNA may be transcribed leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specifity for miRNA/miNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. NUCLEIC ACID

Nucleic acids are provided herein. The nucleic acid may comprise the sequence of SEQ ID NOS: 1-21 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

| miR name | MID | HID |
|---|---|---|
| hsa-miR-182 | 1 | 7 |
| hsa-miR-29a | 2 | 9 |
| hsa-miR-100 | 3 | 10 |
| hsa-miR-199b | 4 | 11 |
| hsa-miR-96 | 5 | 12 |
| hsa-miR-335 | 6 | 13 |
| hsa-miR-183 | 8 | 14 | miR name: is the miRBase registry name (release 9.2).
MID: is the SEQ ID NO of the mature microRNA.
HID: is the SEQ ID NO of the microRNA hairpin precursor (Pre-microRNA).

a. Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al (Nature Biotechnology 2005; 23:709-17) and Rossi (Nature Biotechnology 2005:23; 682-4), the contents of which are incorporated herein by reference. The protamine-fusion protein may comprise the abundant and highly basic cellular protein protamine. The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

b. Pri-miRNA

The nucleic acid may comprise a sequence of a pri-miRNA or a variant thereof. The pri-miRNA sequence may comprise from 45-30,000, 50-25,000,100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-14 or variants thereof.

The pri-miRNA may form a hairpin structure. The hairpin may comprise first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

c. Pre-miRNA

The nucleic acid may also comprise a sequence of a pre-miRNA or a variant thereof. The pre-mIRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-14 or variants thereof.

d. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-6, 8 or variants thereof.

e. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-6, 8 or variants thereof.

f. Binding Site of Target

The nucleic acid may also comprise a sequence of a target miRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the complementarity sequence of SEQ ID NOS: 1-6, 8.

4. Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

A host cell is also provided comprising a vector, synthetic gene or nucleic acid described herein. The cell may be a bacterial, fungal, plant, insect or animal cell. For example, the host cell line may be DG44 and DUXB1 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

7. Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

8. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. Compositions

A pharmaceutical composition is also provided. The composition may comprise a nucleic acid described herein and optionally a pharmaceutically acceptable carrier. The composition may encompass modified oligonucleotides that are complementary to any nucleobase sequence version of the miRNAs described herein or a precursor thereof.

In certain embodiments, a nucleobase sequence of a modified oligonucleotide is fully complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA to which it is complementary.

In certain embodiments, the number of linked nucleosides of a modified oligonucleotide is less than the length of the mature miRNA to which it is complementary. In certain such embodiments, the number of linked nucleosides of a modified oligonucleotide is one less than the length of the mature miRNA to which it is complementary. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence that is fully complementary to a portion of a miRNA sequence.

In certain embodiments, a modified oligonucleotide consists of 15 to 30 linked nucleosides. In certain embodiments, a modified oligonucleotide consists of 19 to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Modified oligonucleotides of the present invention comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, 2'-O-methyl group is present in the sugar residue. Alternatively, oligonucleotides could be complexed to lipids or protein carriers, including cholesterol, liposomes, antibody protomer fusions, cyclodextrin nanoparticles, fusogenic pepfides, aptamers, biodegradable polyactide copolymers, and polymers. Positively charged cationic liposomes and polymers, such as polyethyleneimine, are currently the two major carriers used to complex with negatively charged oligonucleotides for systemic delivery.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical composition is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising modified oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention are formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

10. Therapeutic

A method for treating melanoma is also provided. Furthermore, existing miRNA or anti-miRNA molecules may be used as starting materials for the manufacture of sequence-modified anti-miRNA molecules. As previously discussed the methods, compositions and articles of manufacture of the present invention are particularly useful in the treatment of melanoma.

The compositions of the present invention may be combined with a chemotherapeutic agent, a combination of chemotherapeutic agents and/or a radiotherapy.

Cancer treatments often comprise more than one therapy. As such, in certain embodiments the present invention provides methods for treating melanoma comprising administering to a subject in need thereof a composition comprising a modified oligonucleotide complementary to a miRNA, or a precursor thereof, and further comprising administering at least one additional therapy.

In certain embodiments, an additional therapy may also be designed to treat melanoma. An additional therapy may be a chemotherapeutic agent. Suitable chemotherapeutic agents include dacarbazine (DTIC), hydroxylurea, temozolomide, 5-fluorouracil, gemcitabine, doxorubicine, mitomycin c, sorafenib, etoposide, carboplatin, epirubicin, irinotecan and oxaliplatin. An additional suitable agent includes a modified oligonucleotide, other than a modified oligonucleotide of the present invention that is used to treat cancer. An additional therapy may be surgical resection of tumor(s), or chemoembolization.

11. Diagnostic

A method of diagnosis is also provided. The method comprises detecting a differential expression level of melanoma-associated nucleic acid in a biological sample. The sample may be derived from a patient. Diagnosis of a disease state in a patient may allow for prognosis and selection of therapeutic strategy. Further, the developmental stage of cells may be classified by determining temporarily expressed melanoma-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the nucleic acids which indicate the diagnosis may differ from those which indicate the prognosis and molecular profiling of the condition of the cells may lead to distinctions between responsive or refractory conditions or may be predictive of outcomes.

12. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

Having now generally described the invention, the same will be more readily understood through reference to the following examples, which are provided by way of illustration and are not intended to be limiting of the present invention.

EXAMPLES

Example 1

Materials and Methods

Cell lines. SK-MEL-19, -29, -85, -94, -100, -103, -147, -173, -187, -192, -197 melanoma cell lines were kindly provided by Dr. Alan Houghton (MSKCC) and Hermes cells by Dr. Bennett (UCL); 501 MEL were obtained from Yale University. HEK293T and A375 cells were obtained from ATCC. The B16F10 mouse melanoma cell line and the primary human melanoma cells WM 278 and WM 1552C were a gift of Dr. Orlow (NYU). Human melanocytes were purchased from Lonza (adult and neonatal) and Yale University. Most SK-MEL cell lines were cultured with MEM (Cellgro,10-010) supplemented with 10% Fetal Bovine Serum (Sigma, F2442), 1% non-essential aminoacids (Gibco, 11140) and 1% Penicillin/Streptomycin (Cellgro, 30-001) and maintained at 37° C. in a saturated humidified atmosphere and 5% $CO_2$. Melanocytes and Hermes were cultured with Medium 254 (Cascade Biologics, M-254) supplemented with 20WnM TPA Tetradecanoyl phorbol acetate (TPA; Sigma, P1585). WM cells were cultured with MEL 2% melanoma growth medium (Hsu M Y, Elder D E, Herlyn M. Melanoma: the Wistar (WM) melanoma cell lines. In: Masters J R W, Palsson B, editors. Human cell culture. London: Kluwer Academic Publisher; 1999. p. 259-74) which consists of 4:1 MCDB 153 (Sigma, M7403) and L15 medium (Cellgro, 10-045), supplemented with 2% Fetal Bovine Serum (Sigma, F2442), 5 ug/mL insulin (Sigma, 16634), 15 ug/mL bovine pituitary extract (Upstate, $O_2$-103), 1.68 mmol/L calcium chloride, and 5 ng/mL EGF (BD, 354001).

Real-time quantitative PCR (qRT-PCR). Total RNA was extracted using the mirVana microRNA extraction kit (Ambion) or the miRNAeasy Mini Kit (Qiagen). qRT-PCR analysis of mir-29a, mir-100, mir-182, mir-199b, mir-96, and mir-335 was performed by using miRNA-specific mirVana qRT-PCR Primer set (Ambion) or miScript Reverse Transcription Kit and miScript SYBR Green PCR kit (Qiagen) (hsa-miR-182, -183, -96, -182*, mmu-miR-182). For the Ambion system, total RNA was reversed transcribed using the corresponding mirVana RT Primer and the mirVana microRNA Detection kit (Ambion). PCR was performed on RT products by adding the mirVana PCR primers and the SYBR Green master mix (Ambion), supplemented with Taq DNA polymerase (Sigma). For the Qiagen system, 1 g total RNA was reverse transcribed using the miScript RT kit (Qiagen). The generated cDNA was used as input in the miScript SYBR Green PCR kit (Qiagen). Both melting curve analysis and agarose gel electrophoresis were used to confirm the specificity of the amplification reactions. Fold changes were Log 2 transformed for generation of heat maps. MiR-24, U6, or 5S were used for normalization of input RNA/cDNA levels.

Plasmids. To generate a mir-182 expression vector, a ~200 bp genomic fragment up and downstream of the pre-mir-182 (SEQ ID NO: 7) form was amplified by PCR [primers: Forward 5'-TGCCCTAGGGATGGTGTCT-3' (SEQ ID NO: 15) and Reverse: 5'-CCCTCACTCCTCGATTCAGA-3' (SEQ ID NO: 16)] and cloned it into pCR2.10 TOPO vector (Invitrogen. Retroviral constructs were obtained by digesting the TOPO construct with EcoRI and subcloning it into pMSCV-PURO-IRES-GFP (MSCV-PIG) vector (a gift of Dr. Lowe, CSHL). Alternatively, a 15 lbp-fragment [Primers: Forward 5'-CAGAAGGGTTAACAAGGCCTCCCCAGCTCCTGG-3' (SEQ ID NO: 17) and Reverse: 5'-CGCCTCGAGC-CTCGCTGGCTGTGCACA-3' (SEQ ID NO: 18)] containing strictly the pre-miR-182 form was cloned into pGIPZ or pTRIPZ (Open Biosystems). A 3' UTR region of FOXO3A was amplified by PCR of genomic DNA using the following primers: Forward, 5'-CTCGAGTCACTGAGGAAGGG-GAAGTG-3' (SEQ ID NO: 19) and Reverse, 5'-GCGGC-CGCTGTGCTAATCAGAGCATCGTT-3' (SEQ ID NO: 20) and cloned into pCR2.1 TOPO (Invitrogen) and subcloned into psiCHECKTM-1 Vector (Promega, Madison, Wis., USA) downstream of the *Renilla* luciferase cDNA. All vectors were sequenced to confirm insert direction and sequence identity. The amplified FOXO3 3' UTR had the following sequence (SEQ ID NO: 21):

```
AGGATCACTGAGGAAGGGGAAGTGGGCAAAGCAGACCCTCAAACTGACAC
AAGACCTACAGAGAAAACCCTTTGCCAAATCTGCTCTCAGCAAGTGGACA
GTGATACCGTTTACAGCTTAACACCTTTGTGAATCCCACGCCATTTTCCT
AACCCAGCAGAGACTGTTAATGGCCCCTTACCCTGGGTGAAGCACTTACC
CTTGGAACAGAACTCTAAAAAGTATGCAAAATCTTCCTTGTACAGGGTGG
TGAGCCGCCTGCCAGTGGAGGACAGCACCCCTCAGCACCACCCACCCTCA
TTCAGAGCACACCGTGAGCCCCCGTCGGCCATTCTGTGGTGTTTTAATAT
TGCGATGGTTTATGGGACGTTTTAAGTGTTGTTCTTGTGTTTGTTTTCCT
TTGACTTTCTGAGTTTTTCACATGCATTAACTTGCGGTATTTTTCTGTTA
AAATGTTAACCGTCCTTCCCCTAGCAAATTTAAAAACAGAAAGAAAATGT
TGTACCAGTTACCATTCCGGGTTCGAGCATCACAAGCTTTTGAGCGCATG
GAACTCCATAAACTAACAAATTACATAAACTAAAGGGGGATTTTCTTTCT
TCTTTTGTTTGGTAGAAAATTATCCTTTTCTAAAAACTGAACAATGCCAC
AATTGTTTGCTATGTGCACCCGTCCAGGACAGAACCGTGCATAGGCAAAA
GGAGTGGAGCACAGCGTCCGGCCCAGTGTGTTTCCGGTTCTGAGTCAGGG
TGATCTGTGGACGGGACCCCAGCACCAAGTCTACGGGTGCCAGATCAGTA
GGGCCTGTGATTTCCTGTCAGTGTCCTCAGCTAATGTGAACAGTGTTGGT
CTGCTGGTTAGAAACTAGAATATTGATATTTTCAGGAAAGAAATCAGCTC
AGCTCTCCACTCATTGCCAATGTCACTAAAGGGTTTAGTTTTAAGGAGAA
AGAAAAGGAAAAAAAAAAAAAACA
```

Viral-mediated gene transduction. Anphotropic retroviruses were produced using described methods (Hernando et al., 2004). Briefly, packaging HEK293T (Phoenix) cells were transfected with 20 µg of MSCV-derived vectors by the calcium phosphate method (Cullen, 1987). Supernatants were filtered through 0.45 µm filters. Melanoma cells were transduced with retroviral supernatants supplemented with 2 µg/ml polybrene, and pools of cells stably transduced were selected by adding 2 µg/ml Puromycin to the culture medium (Gibco/Invitrogen).

Lentiviruses were propagated using previously described methods (Naldini et al., 1996; Zufferey et al., 1998). Briefly, HEK293T cells were seeded at a density of $2.5 \times 10^6$ cells in 100 mm dishes. The following day, cells were transfected with 20 µg of pGIPZ or pTRIPZ derived constructs, 13 µg of pSPAX2, and 7 µg of pM2G. The transfection was routinely performed by calcium phosphate. After 48 h, viral supernatant was collected and filtered, using 0.45 µm filters. When concentration was needed, viral supernatant was centrifuged at 50,000×g for 120 mm.

In vitro Transformation Assays.

Growth curves. A time-course of MSCV-PIG and MSCV-PIG-miR182 was generated by seeding $2 \times 10^4$ cells in M12-well (n=4). At indicated times, cells were fixed with 1% glutaraldehyde and stained with crystal violet. After extensive washing, crystal violet was resolubilized in 15% acetic acid and absorbance was measured at 595 nm. Values were represented as the percentage of cell growth with respect to day 0. Clonability. Cells were seeded at low density and allowed to grow for 10 days. Then, cells were fixed with 1% glutaraldehyde and stained with 0.5% crystal violet. After extensive washing, colonies were photographed and scored.

Growth in soft agar. Cells were plated in MEM plus 10% FBS and 1% non-essential amino acids in 0.33% (w/v) noble agar on top of a 0.5% noble agar bottom layer. Cells were fed weekly by the addition of fresh media. After two weeks, colonies were stained with 0.05% crystal violet, photographed and scored.

Invasion and Migration Assays.

Wound-healing assays. An artificial "wound" was created using a 10 µl pipette tip on a confluent cell monolayer growing on M6-well plates in complete medium. Photographs were taken at the indicated times using an inverted microscope (Zeiss).

Fibronectin transwell invasion assay. A modification of the method described in Dewhurst et al (1997) was used to study the effect of miR-182 on the invasion of the melanoma cells through a layer of human fibronectin. Briefly, a suspension of $2.5 \times 10^5$ A375 or $6 \times 10^5$ SK-MEL-19 melanoma cells (contained in 300 µl of basal media) was added to cell culture inserts (Falcon) containing a polycarbonate filter with 8 µm diameter pores covered with fibronectin (100 mg/ml) and 2.5% BSA. Cells were incubated for the indicated times under standard culture conditions. Tumor cells remaining on the top-side of the membrane were removed and cells that had migrated to the under side were fixed and stained with crystal violet. Five preset fields per insert were photographed and scored.

In vivo metastasis assay. Subconfluent cultures of stably transduced B16F10 cells (MSCV-PIG or MSCV-PIG-miR182) were harvested, washed and resuspended in PBS. BALB/c mice (5 mice per group) were injected intravenously with tumor cells ($1.5 \times 10^5$/100 µl/mouse). After 10 days, mice were sacrificed, lungs removed and fixed, and the number of isolated and discrete pigmented lung surface lesions counted on each lobe of every specimen. Tissues were paraffin-embedded, and 5 µm sections were H&E-stained (hematoxylin/eosin) H&E-stained.

Cell death assays. A375 and SK-MEL-19 melanoma cells ($5 \times 10^4$ cells/well) were seeded in 12-well plates. 24 h later, cells were transfected with 150 nM of miRIDIAN anti-miRI82 or miRIDIAN microRNA inhibitor negative control oligonucleotides (Dharmacon) by triplicate. 48 h later, cells were harvested and cell death was analyzed by trypan blue exclusion method. Alternatively, nuclei were stained for 20 min with 0.05 µg/ml of Hoechst 33342 at the indicated times. Uniformly stained nuclei were scored as healthy, viable cells, whereas condensed or fragmented nuclei were scored as apoptotic. Experiments were repeated three times and no less than 500 cells were counted per condition.

Western Blotting. Cell lysates were harvested with 2% sodium dodecyl sulfate (SDS)-125 mM Tris/HCl pH 7.4 and protease inhibitors (Roche) and protein concentration was quantified by a modified Lowry assay (Bio-Rad Dc protein assay, Bio-Rad). Cell lysates (25-30 µg of protein) were resolved in Tris/glycine SDS/PAGE gels and transferred to nitrocellulose or PVDF membranes (Invitrogen) using a semi-dry IBlot™ transfer unit (Invitrogen). After blocking with PBS-T (0.1% Tween-20 PBS) containing 5% non-fat dry milk for 1 h at room temperature, membranes were probed with the appropriate primary antibodies overnight at 4° C. [FOXO3 1:1000 (Upstate 07-702), Foxo1 1:500 (Cell Signalling 9454), p18 INK4c 1:500 (Genetex GTX14974), Caspase2 1:500 (Alexis ALX-804-356), Caspase2 1:1000 (Cell Signalling 9665), MITF 1:1000 (Sigma M6065), Ran 1:1000 (Santa Cruz sc-1156), Tubulin 1:5000 (Sigma T9026)]. Membranes were washed in PBS-T followed by 1 h incubation with the corresponding peroxidase-conjugated secondary antibodies. Membranes were developed with the ECL Plus Western blotting detection kit (GE Healthcare Bio-Sciences Corporation, Piscataway, N.J., USA).

Luciferase assay. miR-182 and empty-vector infected A375 cells were seeded into M6-well plates and 24 h later were transfected with the psiCHECK2-FOXO3 3'UTR vector and incubated 24 h more in presence or absence of doxocycline. Alternatively, HEK293T or SK– MEL-19 were seeded into 96-well plates and co-transfected with psiCHECK2-FOXO3 3'UTR (0.1 µg) vector and 2, 20 and 200 nM of miR-182 mimic or miRIDIAN microRNA mimic Negative control (Dharmacon). Luciferase activity was measured using the Dual-Glo™. Luciferase Assay System (Promega) following slightly modified manufacturer's instructions. Renilla luciferase activity was normalized to corresponding firefly luciferase activity and plotted as a percent of control.

In situ Hybridization.

Tissue microarray slides including triplicates of 26 primary, 28 metastatic (unpaired) human melanomas, and 15 human normal skin and control tissues (formalin fixed, paraffin-embedded) were purchased from Biomax (ME207). Deparaffined and deproteinizated sections were pre-hybridized by incubation for 1-3 h at 52° C. in hybridization solution (50% formamide, 5×SSC, 0.1% Tween-20, 9.2 mM citric acid pH6, 50 µg/ml heparin, 0.5 mg/ml yeast RNA). Hybridizations were performed overnight at 52° C. following the addition of 50 nM DIG-labeled locked nucleid acid (LNA)-based probes specific for mir-1 82 and U6 (Exiqon), denatured for 2 min at 95° C. Sections were extensively washed at 52° C. three times with 5×SSC and twice with 0.2×SSC and subsequently blocked for 2 h in blocking solution (0.5% BSA, 10% heat inactivated sheep serum, 0.1% Tween-20), Then, sections were incubated overnight with anti-DIG-AP Fab fragment (Roche) in blocking buffer. Alkaline phosphatase activity was detected using BM Purple AP Substrate (Roche) by incubation for 2-24 h at 25° C. Reactions were terminated for 1 h in 10 mM EDTA in PBS (pH 5.5). Slides were mounted in glycerol under glass coverslips. Scoring melanoma cores was restricted to the tumor cells. ISH results were semiquantitatively graded according to the intensity of staining and scored from 1 to 4, and then normalized to U6 levels (as internal control).

Microarray and Statistical Analyses.

SK-MEL-19 and SK-MEL-29 cells were transduced with pGIPZ-scrambled (SCR) and pGIPZ-miR-182 lentiviral vectors, and cells collected 24 h and 48 h post-infection. 1.5 ug of RNA per time point were labeled and hybridized on Affymetrix U133a chips containing ~22000 probes. Raw data from Affymetrix array scans was processed using the Bioconductor package affy and the R language for statistical computing (Bioconductor, 2007). The data were normalized using the RMA method of (Irizarry et al., 2003). Genespring (GS) software was used to determine differentially expressed (1.25 fold decreased) genes between miR-182 and vector-transduced cells in both SK-MEL-19 and SK-MEL-29 at 48 h of which there were 201 genes represented by 219 probes. The Venn diagram feature of GS was used to compare miR-182 predicted targets with this list of 219 probes. For miR-182 target predictions, miRanda generated 927 probes, Targetscan generated 1001 probes, and Pictar generated 1058 probes represented on the U133a platform. All statistical analysis was performed using number of probe sets as opposed to genes to account for variations in replicate numbers.

Example 2 mir-182 is Over-expressed in Human Melanoma Cell Lines and Tissues

Figure 1B:
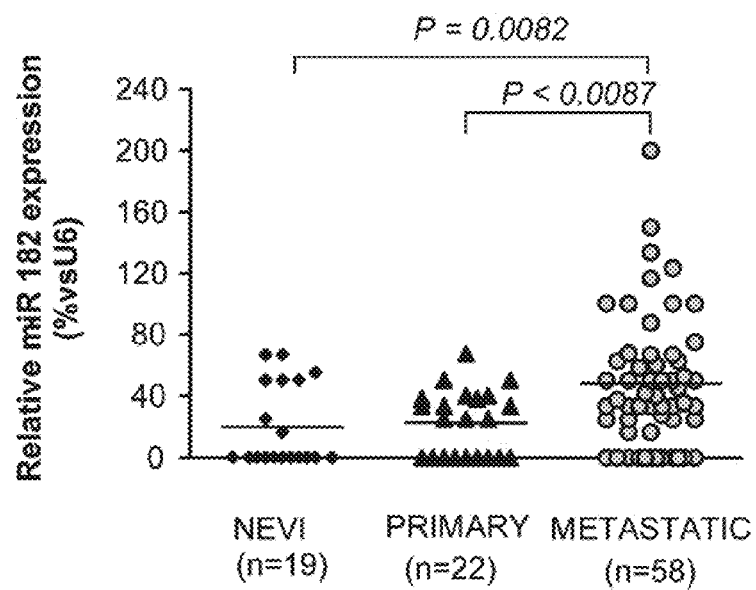
Figure 1C:
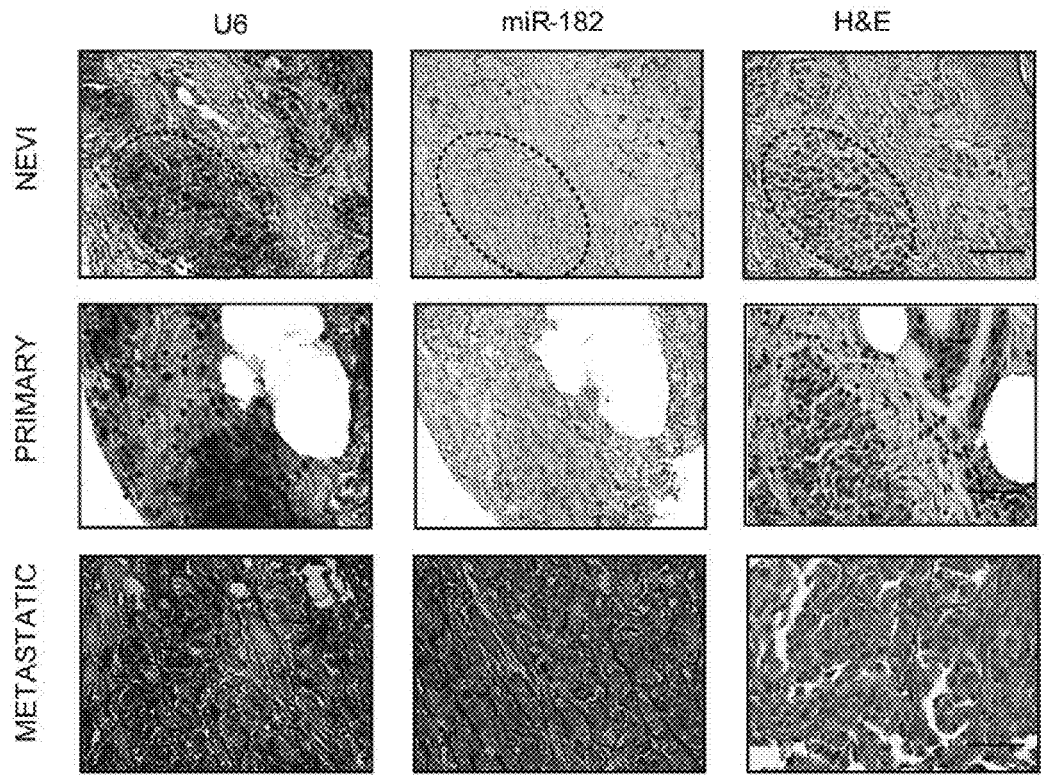

In order to identify miRNAs whose deregulation might participate in melanoma pathogenesis, we selected potential candidates among those characteristic of melanoma cells (Gaur et al., 2007) which are located in genomic regions frequently gained or lost in metastatic melanoma (Zhang et al., 2006). We analyzed their expression in a subset of 3 human melanocyte primary cultures and 11 metastatic melanoma cell lines, by quantitative RT-PCR. Remarkably, among 6 miRNAs analyzed, miR-182 was found over-expressed at various levels in almost all metastatic cell lines compared to primary human melanocytes (FIG. 1A). In situ hybridization (ISH) on a tissue microarray containing a large cohort of melanoma tissues confirmed that the majority of melanomas express higher levels of miR-182. Interestingly, although a slight enrichment in miR-182 positive cases was observed in the metastatic group, most primary cases analyzed already exhibited high miR-182 levels (FIG. 1B-C).

Figure 5D:
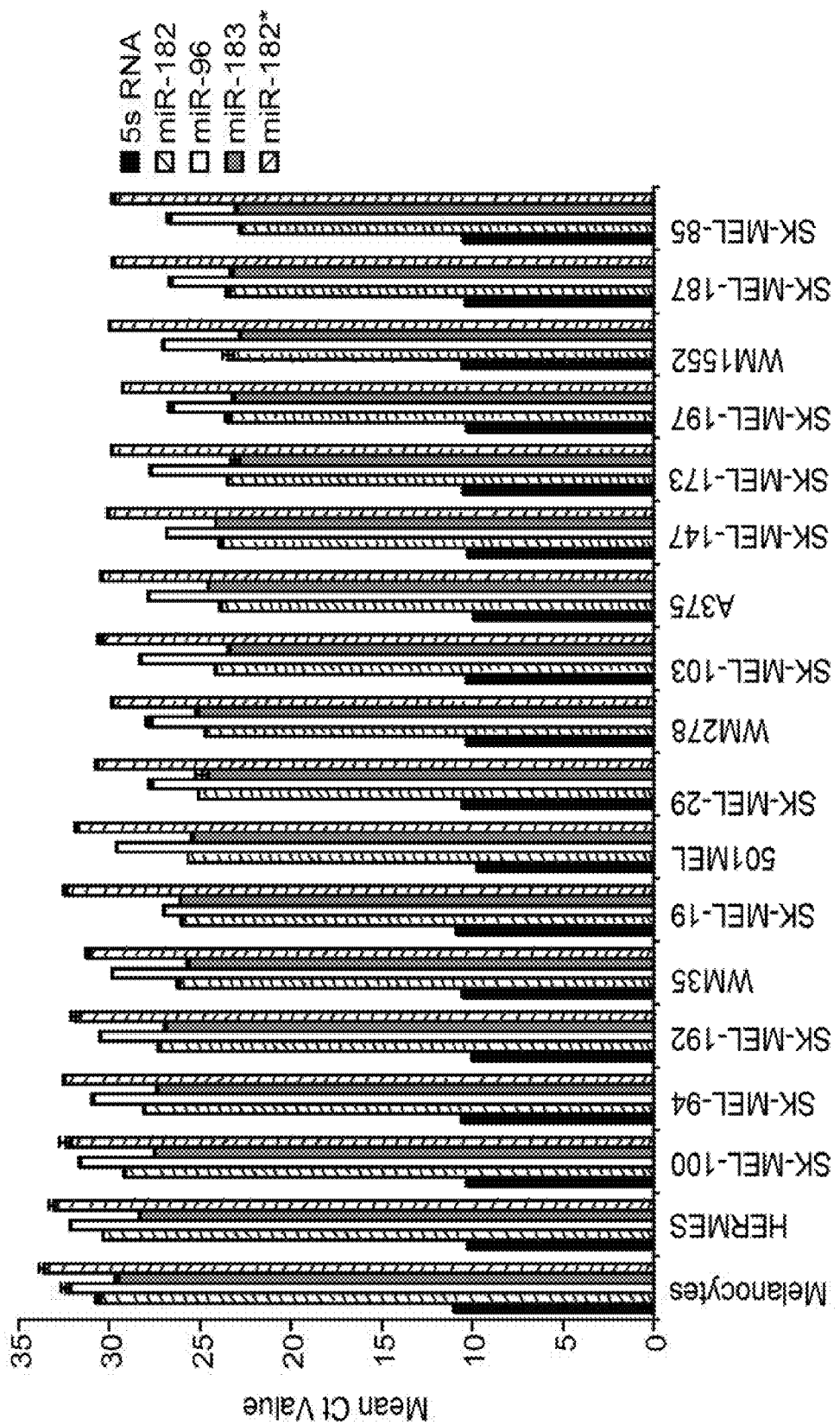
FIG. 5 shows that miR-182 belongs to a miRNA gene cluster. (A) Schematic diagram of the mature sequences of cluster components miR-182, 96 and -183. (B) Mature miRNA sequences of miR-182 (SEQ ID NO: 1), miR-96 (SEQ ID NO: 5) and miR-183 (SEQ ID NO: 8). (C) Pre-miRNA sequences of miR-182 (SEQ ID NO: 7), miR-96 (SEQ ID NO: 12) and miR-183 (SEQ ID NO: 14). (D) Quantitative RT-PCR of mature miR-182 (SEQ ID NO: 1), miR-96 (SEQ ID NO: 5) and miR-183 (SEQ ID NO: 8) levels in a panel of primary and metastatic melanoma cell lines, compared to normal melanocytes.

It has been recently described that miR-182 forms a gene cluster with two adjacent miRNAs (miR-96 and miR-183) (Landgraf et al., 2007; Xu et al., 2007) which have highly homologous 5'-seed sequences (FIG. 5B-C). We analyzed whether the expression of these miRNAs encompasses that of miR-182 in the same set of melanoma metastatic cells and additional primary cell lines. Real time PCR revealed that all three miRNAs show a similar pattern across most cell lines (FIG. 5D), suggesting that the mechanism leading to miR-182 over-expression affects the regulation of the entire cluster. In addition, these data confirmed that abnormal expression of the miR-182/miR-96/miR-183 cluster is already detected in primary melanoma cell lines. Hence, such a molecular event does not seem to be merely a product of the genomic instability inherent to late tumor stages, but rather it may play a role in melanoma initiation or progression.

Figure 6A:
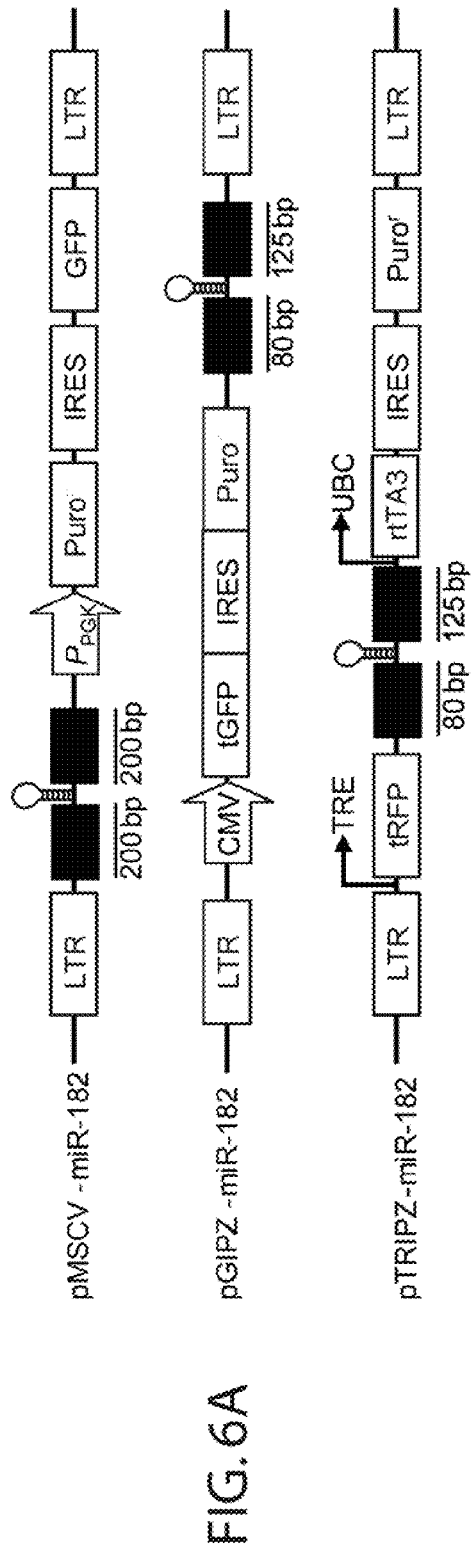
FIG. 6 shows efficient mature miRNA expression driven by retro-lentiviral or liposomal-mediated transduction of melanoma cell lines. (A), Retroviral (MSCV) or Lentiviral (pGIPZ and pTRIPZ) constructs used to deliver miR-182 expression in melanoma cell lines. (B), Gel electrophoresis of RT-PCR products obtained from retroviral transduced SK-MEL-19 melanoma cells (left) and lentiviral A375 transduced cells (middle and right). Total RNA (including small RNAs fraction) was extracted, and mature miR-182 expression was analyzed. U6 was included as a loading control of small RNAs. (C), Representative pictures of transduced SK-MEL-19 and A375 cell lines (bright field [upper left] as indicated by GFP-[lower left], or RFP [lower middle] image), this one after doxocycline addition. Magnification in (C), 40×. Right images shows efficiency of transfection with 200 nM BLOCK-iT Fluorescent Oligo (Invitrogen). Magnification 20×.
Figure 6B:
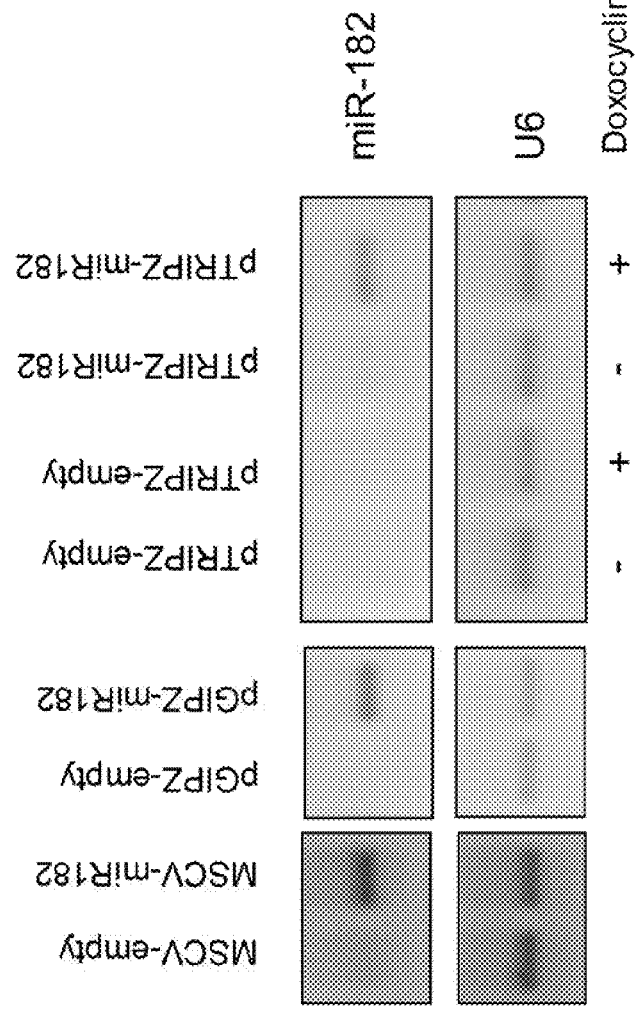
Figure 6C:
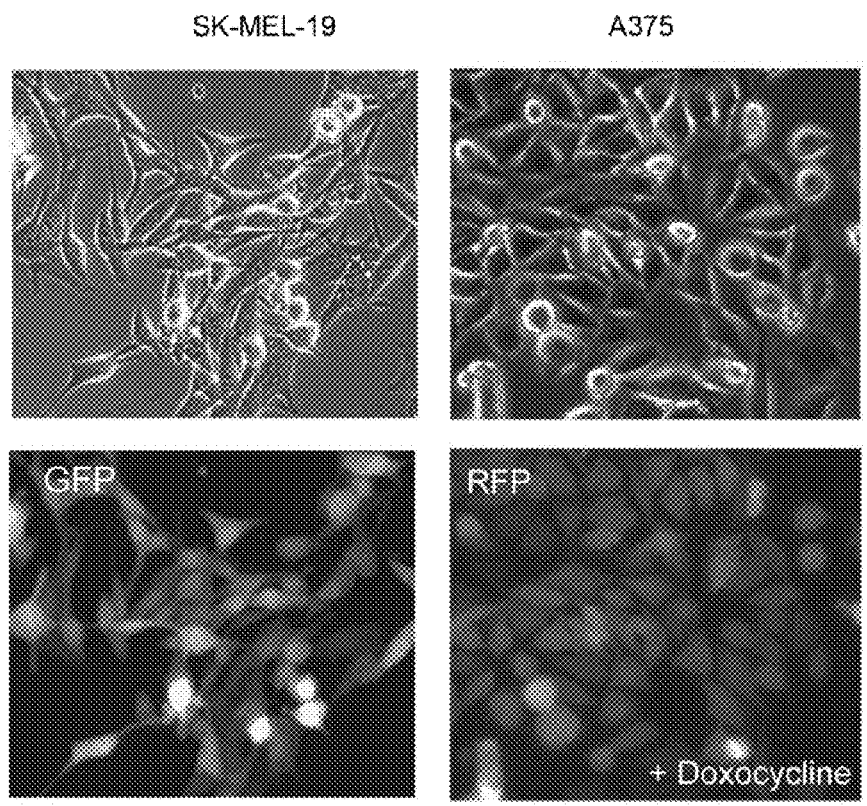
Figure 6D:
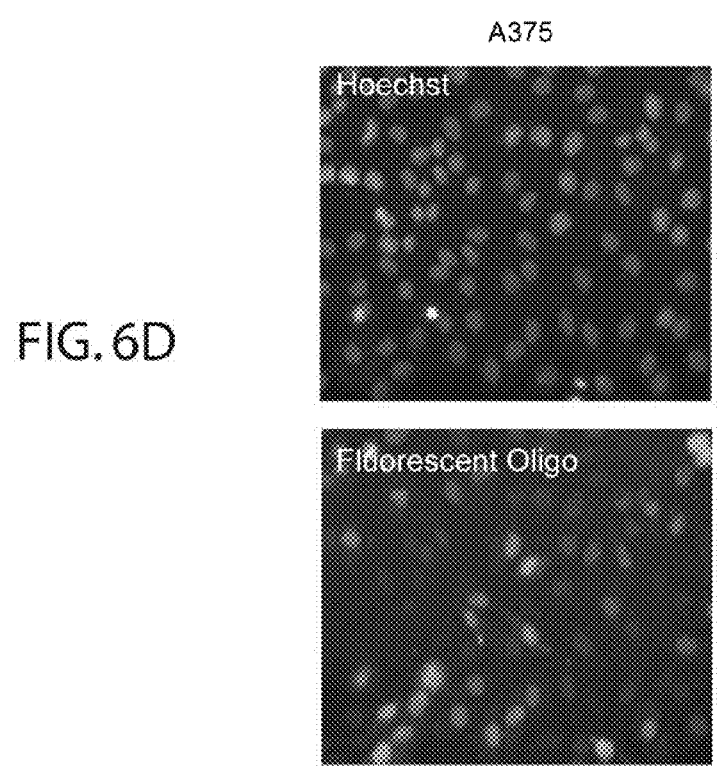

Example 3 hsa-mir-182 Overexpression Enhances the Oncogenic Properties of Human Melanoma Cell Lines We cloned an immature form of miR-182 ('pri-mRNA like'), containing ~200 bp genomic sequence up and downstream of the pre-miR-182 form. This sequence was inserted into a murine stem-cell retrovirus (MSCV)-derived vector (FIG. 6A). Alternatively, we entered the pre-miRNA form (MI0000272) flanked by miR30 sequences into commercial lentiviral vectors pGIPZ and pTRIPZ (FIG. 6A). Previous reports have shown efficient processing of ssRNA sequences from hairpin loops in this context by RNAse III enzymes and the RNAi machinery (Dickins et al., 2005). Indeed, successful expression of the mature form of miR-182 (MI-MAT0000259) from both its endogenous and the artificial miR-30 context was confirmed by RT-PCR (FIG. 6B).

Figure 2A:
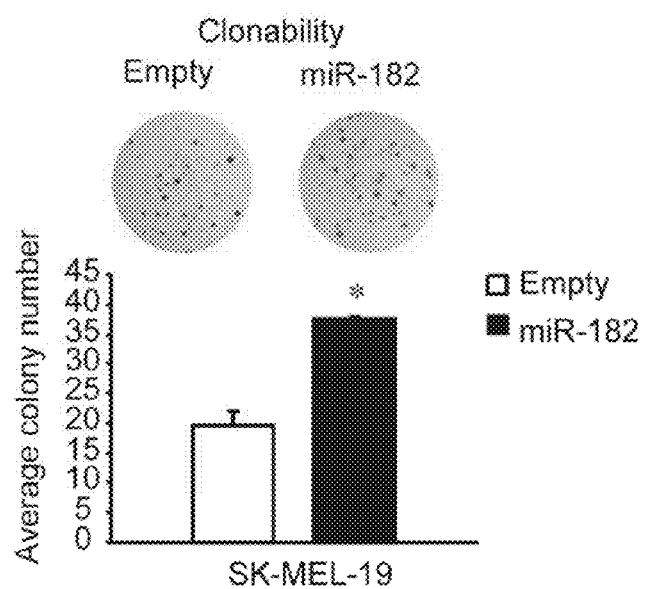
FIG. 2 shows that miR-182 enhances melanoma oncogenic behavior in vitro and in vivo. (A), Colony formation assay. SK-MEL-19 melanoma cells stably transduced with empty vector (Empty) or with hsa-miR-182-expressing vector (miR-182) were seeded at low density and allowed to grow before fixation and staining with crystal violet. Graph is representative of three independent experiments (n=4). (B), Growth in soft agar. Transduced SK-MEL-19 and A375 melanoma cell lines were plated in 0.33% (w/v) noble agar on top of a 0.5% noble agar bottom layer. After 2 weeks, colonies were stained with crystal violet, photographed and scored. (C), Transwell invasion assay of A375 infected with empty vector or miR-182 expressing vector (n=4). (D), Wound-healing assay on SK-MEL-19 stably transduced with either empty vector (Empty) or hsa-miR-182 (miR182). Pictures were taken every 24 hours. Graph represents the width of the remaining open wound calculated in relation to time 0 separation (n=12). (E), In vivo metastasis assay. B16F10 mouse melanoma cells were injected through the lateral tail vein of C57BL/6J mice (n=6). Macroscopic pictures of mice lungs, 10 days post-inoculation. Hematoxylin and eosin (H&E)-stained sections of lung metastases (right; magnification 20×). Arrowheads point to metastatic foci. Histogram with the quantification of large lung metastases. For every assay, a representative experiment is shown in triplicate along with SEM, in (A), (B), and (C). (*$p<0.05$, $p<0.01$, *$p<0.001$).
Figure 2B:
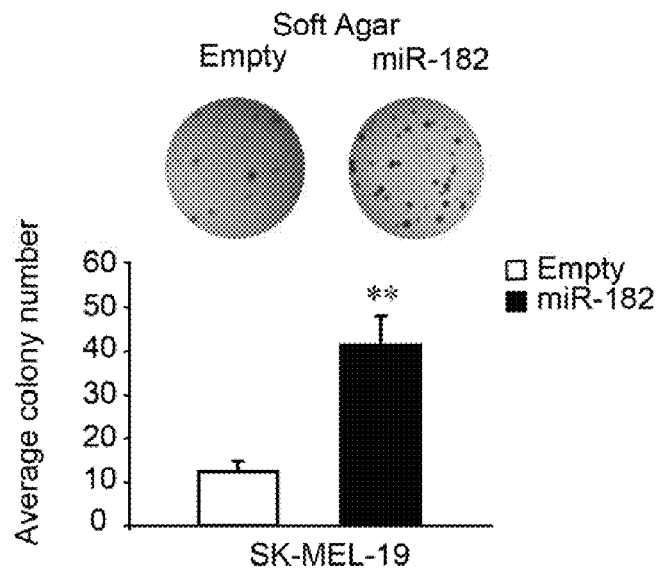

In an attempt to understand the functional effects of miR-182 and explore its potential contribution to melanoma-genesis and/or progression, we exogenously introduced miR-182 into human immortal melanocytes and melanoma cell lines carrying low to moderate miR-182 levels endogenously. MiR-182 over-expression failed to transform human immortal melanocytes (data not shown), but strongly stimulated the oncogenic properties of established melanoma cells. Thus, miR-182 expression increased the ability to form colonies of SK-MEL-19 (FIG. 2A) and SK-MEL-94 cells (data not shown) upon low-density seeding. Moreover, stably transduced melanoma cells (FIG. 2B) showed enhanced anchorage-independent growth, generating more and larger colonies in soft agar. Taken together, these results demonstrate that miR-182 deregulation exacerbates the malignant behavior of human melanoma cells.

Example 4 hsa-miR-182 Positively Regulates Cell Migration and Invasion in vitro

Figure 2C:
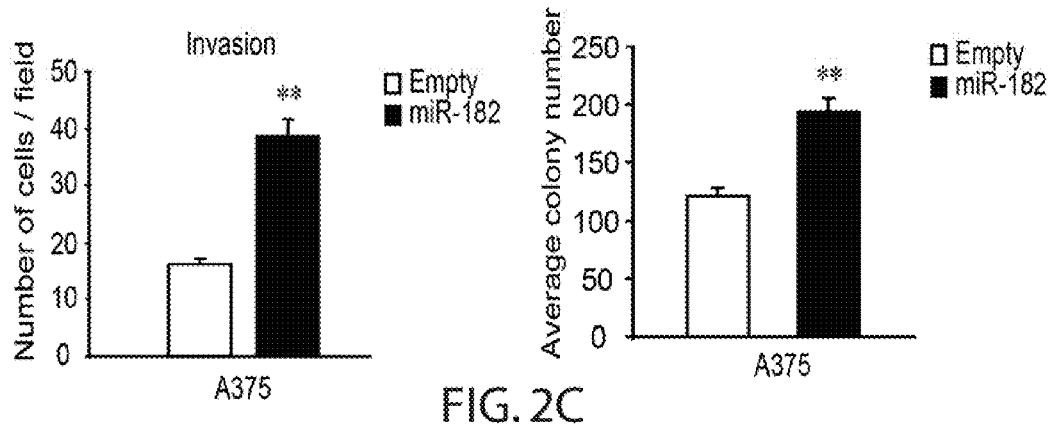
Figure 2D:
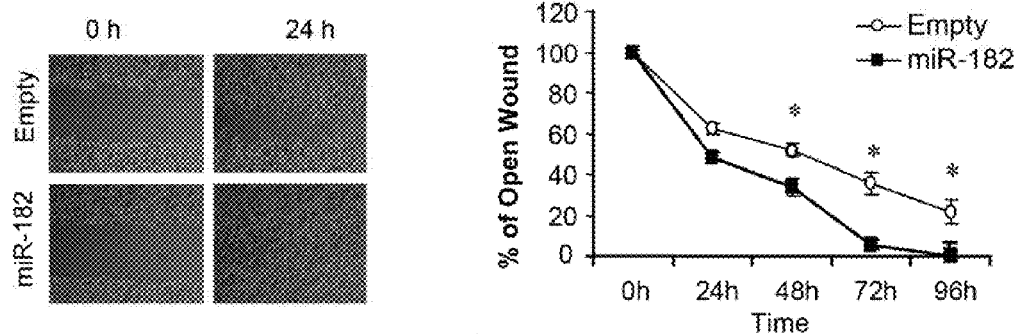

Then we tested whether miR182 activation also promotes cell migration and invasion. Indeed, miR182-expressing cells showed a greater ability to penetrate a fibronectin coat (FIG. 2C), and closed an artificial wound created over a confluent monolayer more quickly than did the equivalent vector-transduced cells (FIG. 2D). To examine whether these properties were, at least in part, explained by increased cell proliferation, we compared the growth rate of miR-182 and vector-transduced cells, but no statistically significant differences were found by means of trypan-blue exclusion, crystal violet staining or WST-1 proliferation assays (data not shown). Therefore, we conclude that miR-182 expression specifically provides to melanoma cells increased mobility through an extracellular matrix, a known requisite for the establishment of metastases.

Example 5 hsa-mir-182 Enhances the in vivo Metastatic Behavior of Melanoma Cells

Figure 2E:
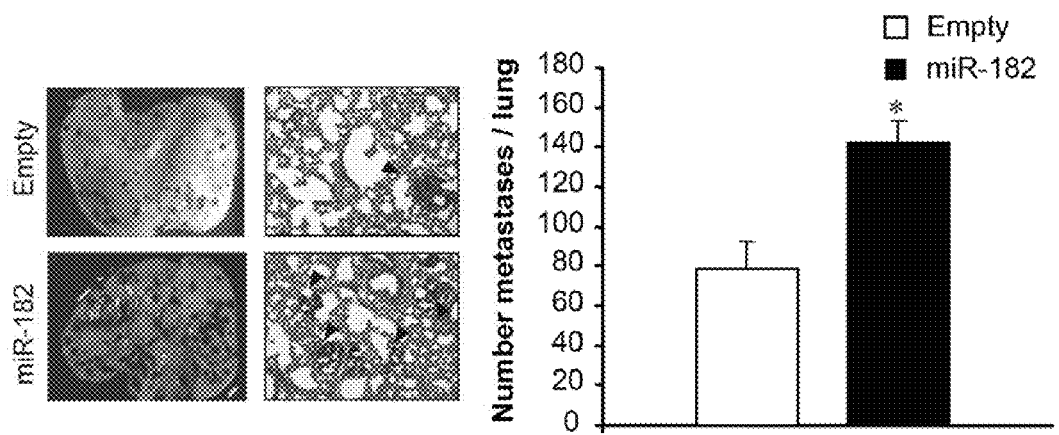

In vitro results led us to study the impact of miR-182 overexpression in a classical in vivo model of melanoma lung metastasis. In this system, B16F 10 mouse melanoma cells were stably transduced with MSCV-empty or MSCV-miR-182 vectors. Mouse cells showed enhancement of oncogenic properties similar to human cells upon miR-182 ectopic expression, assessed by clonability, soft agar and migration assays (FIG. 7). Vector- or miR-182-transduced B16F10 cells were injected into mouse tail veins. Ten days post-injection, mice were sacrificed and lungs photographed and dissected for macro- and microscopic histological examination. Lungs of B16F10-miR-182 injected mice showed a significant increase in the number of large metastases (FIG. 2E), indicating that miR-182 might confer an advantage to melanoma cells in extravasation and/or seeding at a distant location.

In summary, our results demonstrate that the exogenous expression of miR-182 in melanoma cells enhances their malignant behavior, specifically increasing their viability in the absence of cell contact, anchorage-independent growth, and motility in vitro, as well as promoting their in vivo metastatic potential.

Example 6 miR-182 Repression in Melanoma Cells Triggers Cellular Apoptosis

Figure 3A:
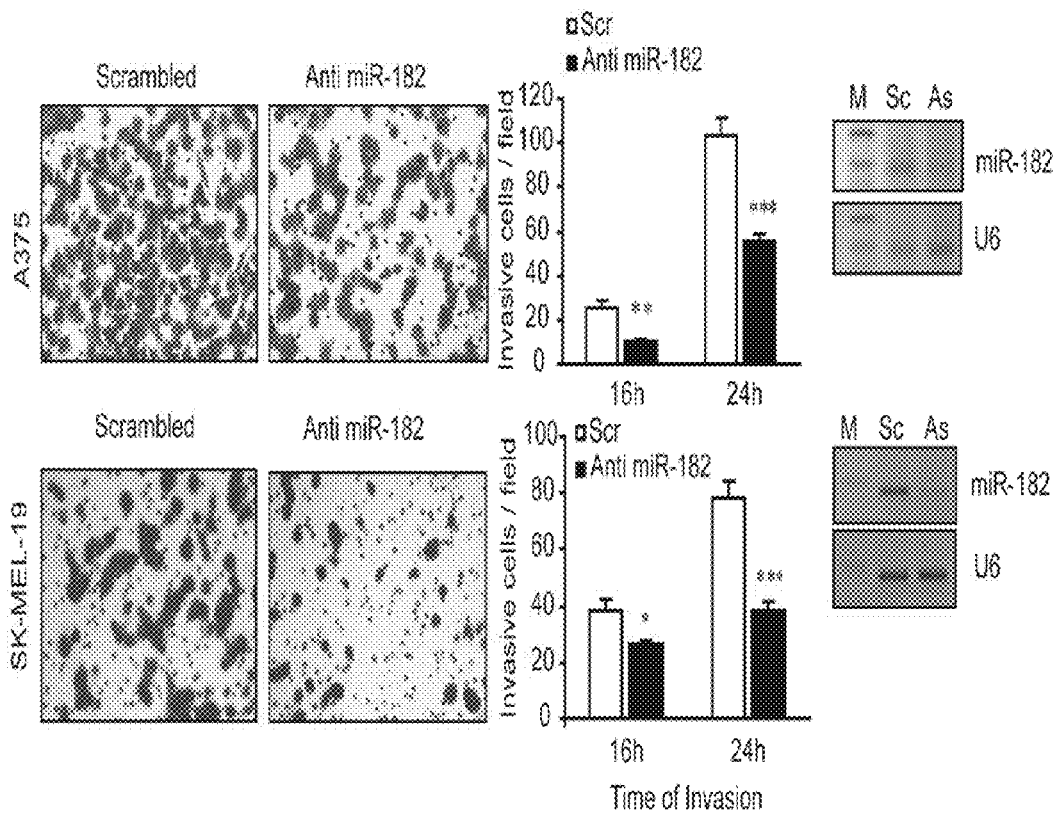
FIG. 3 shows that anti-miR-182 reduces tumor invasiveness and induces apoptosis. (A), Transwell invasion assay on A375 and SK-MEL-19, transfected with 150 nM of scrambled or anti-miR-182 oligonucleotides. Representative images are shown in left panel. Graphs indicate the average number of cells per field at the indicated time points. Right: RT-PCR of miR-182 in A375 (above) or SK-MEL-19 (below) transfected with the inhibitor of miR-182 (As) or a scrambled oligonucleotide (Sc). M, 100 bp DNA ladder. (B), Proliferation assay on A375 and SK-MEL-19 cell lines transfected as in (A). At the indicated times, cells were fixed and stained with crystal violet. Graphs show percentage of proliferation versus time 0. (C), Cell death measured by trypan blue exclusion assay in cells transfected as in (A) or (B), collected and counted after 48 h. (D), Detection of apoptosis in SK-MEL-19 and A375 cells transfected with scrambled or miR-182 inhibitor using nuclear Hoechst staining. Graphs show percentage of condensed or fragmented nuclei. Values in (A), (B), (C) and (D) are representative of three independent experiments±SEM. *$p<0.05$, $p<0.01$, *$p<0.001$. Magnification in (A) and (D), 40×. Magnification of insets in (D), 60×.
Figure 3B:
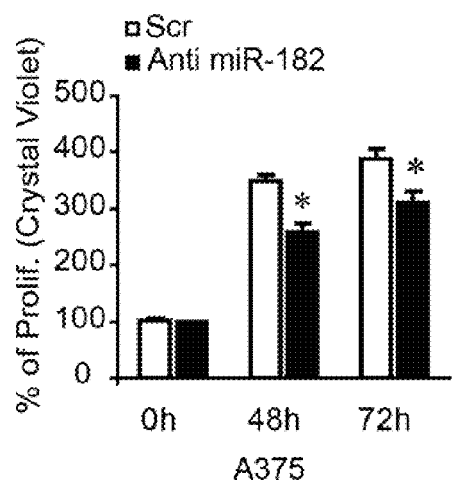
Figure 3B:
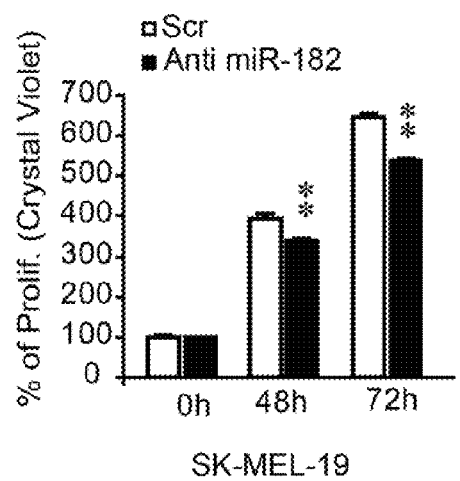
Figure 3C:
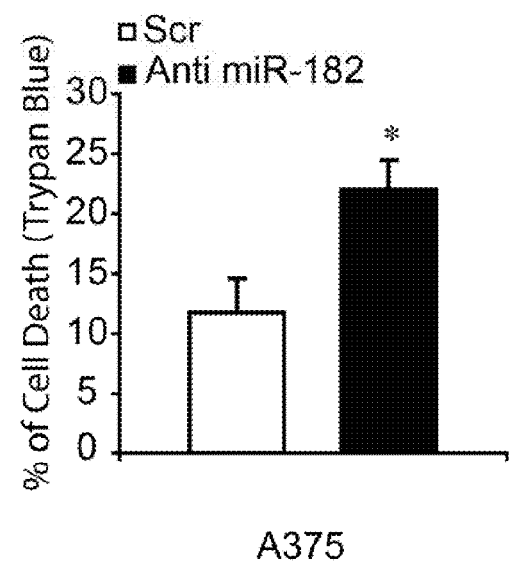
Figure 3C:
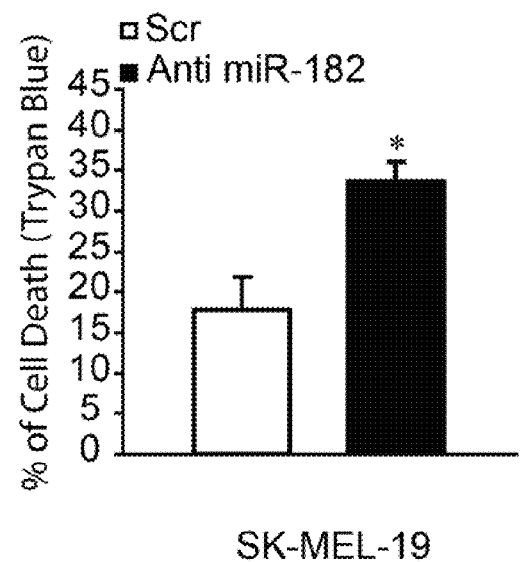
Figure 3D:
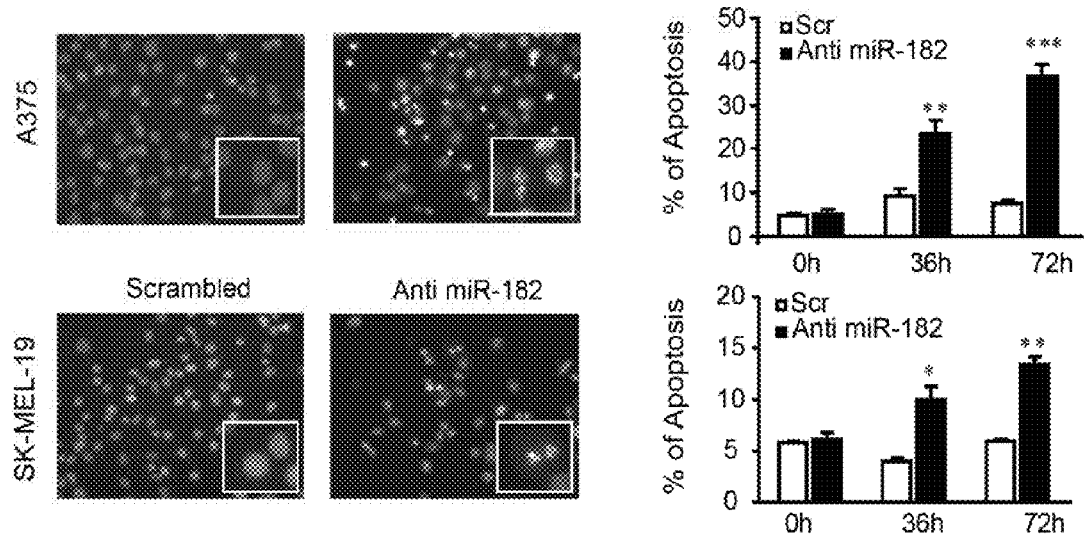

We then conducted in vitro loss-of-function analyses, by transfection of antisense oligonucleotides. Effective miR-182 silencing significantly impaired the invasive potential of melanoma cells in fibronectin invasion assays (FIG. 3A). Moreover, miR-182 targeting remarkably prevented melanoma cell growth (FIG. 3B) by inducing cell death (FIG. 3C). Specifically, by Hoescht staining followed by quantification of cells with condensed and fragmented nuclei, we determined that anti-miR182 treated cells undergo apoptosis (FIG. 3D). Therefore, miR-182 confers a survival advantage to melanoma cells, which may at least partially explain the greater aggressiveness shown in vitro and in vivo by miR-182 transduced cells. Alternatively, miR-182 may be required for the maintenance of viability while cells acquire additional oncogenic properties.

Example 7

Foxo3 and MITF-M are hsa-mir-182 Targets in Melanoma Cells

Figure 4A:
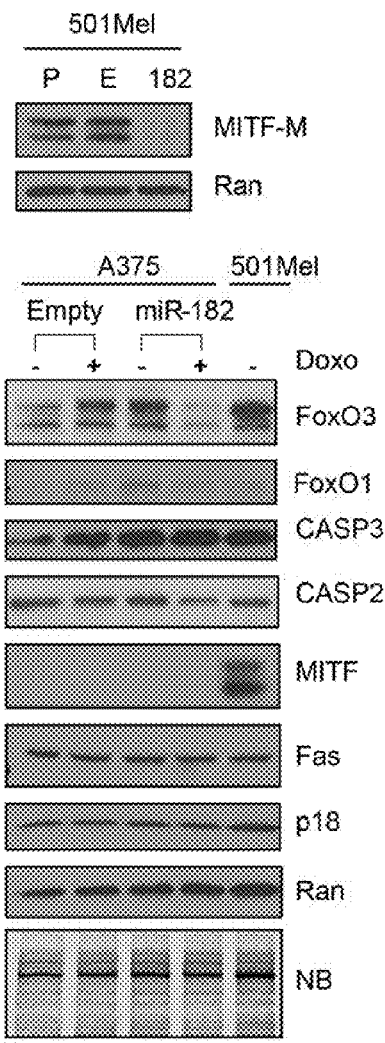
FIG. 4 shows that Foxo3 and MITF are direct and critical miR-182 targets. (A) Western blot analyses of theoretical miR-182 targets in melanoma cell lines, upon vector- and miR-182 exogenous expression (P=parental; E=empty vector). (B) Luciferase assay on HEK293T transfected with increasing amounts of miR-182 mimic oligonucleotides (2, 20, 200 nM) or in (C), co-transfecting mimic miR-182 (2 nM) with increasing amounts of scrambled or anti-miR-182 (20, 200 nM) as indicated. (D) Western blots on A375 cells and SK-MEL-29 cells transduced with anti-miR-182. (E) Invasion assays on A375 and SK-MEL-19 cells transduced with empty vector or shRNAs against Foxo3 or MITF. Efficacy of RNA interference is shown by Western blot. (F) Invasion assays on SK-MEL-19 cells co-infected with lentiviral vectors carrying miR-182 and MITF or Foxo3 cDNAs. Alpha-tubulin and Ran are shown as loading controls. Values in (B), (C), (D) and (E) are representative of three independent experiments±SEM. *$p<0.05$, $p<0.01$, *$p<0.001$.

To identify specific gene targets of miR-182 through which it might promote oncogenic behavior in vitro and in vivo, public algorithms (TargetScan, Pictar, miRANDA) were searched for theoretical target genes whose down-regulation could mediate the observed effects of miR-182. FOXO3 (FKHRL1), FOXO1 (FKHR), MITF, CDKN2C (p18INK4C), CASP3, CASP2, and FAS are all predicted targets, of which only MITF (Microphthalmia-associated Transcription Factor) has been previously validated as controlled by miR-182 during the development of the mouse retina (12). Western blot analysis demonstrated that the M isoform of MITF practically disappears in response to miR-182 up-regulation in 501mel cells (FIG. 4A). Foxo3, Foxo1 and caspase-2 protein levels also diminished in response to hsa-miR-182-induced expression in melanoma cells, while no changes were observed for Fas, caspase-3 or p18Ink4c (FIG. 4A).

Figure 4B:
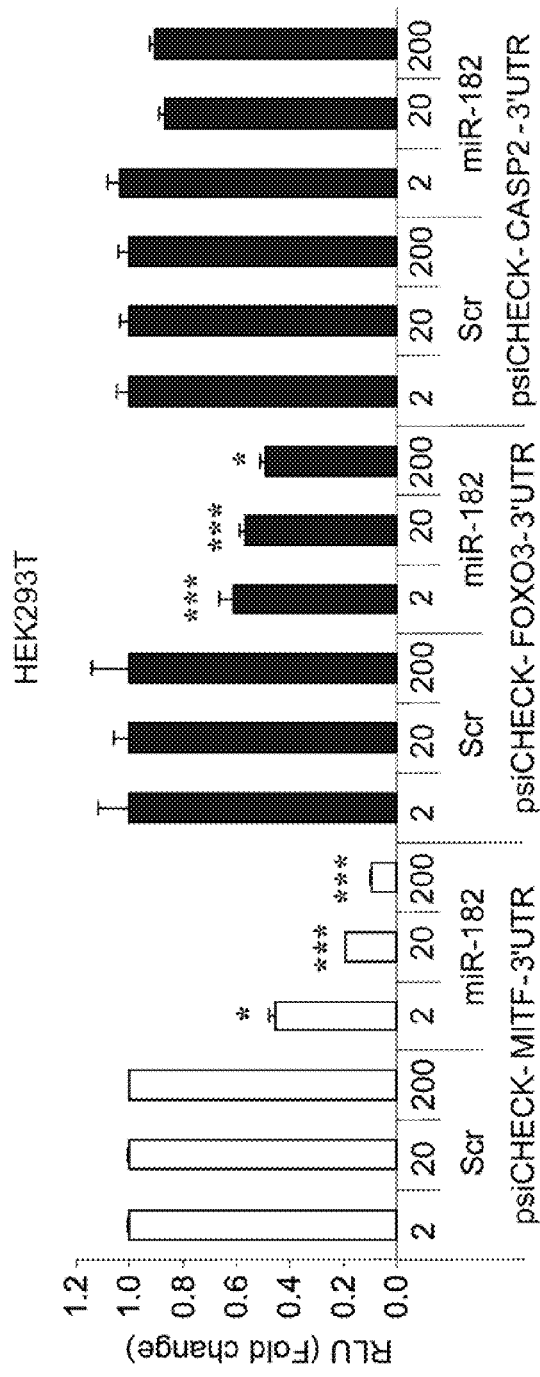
Figure 4C:
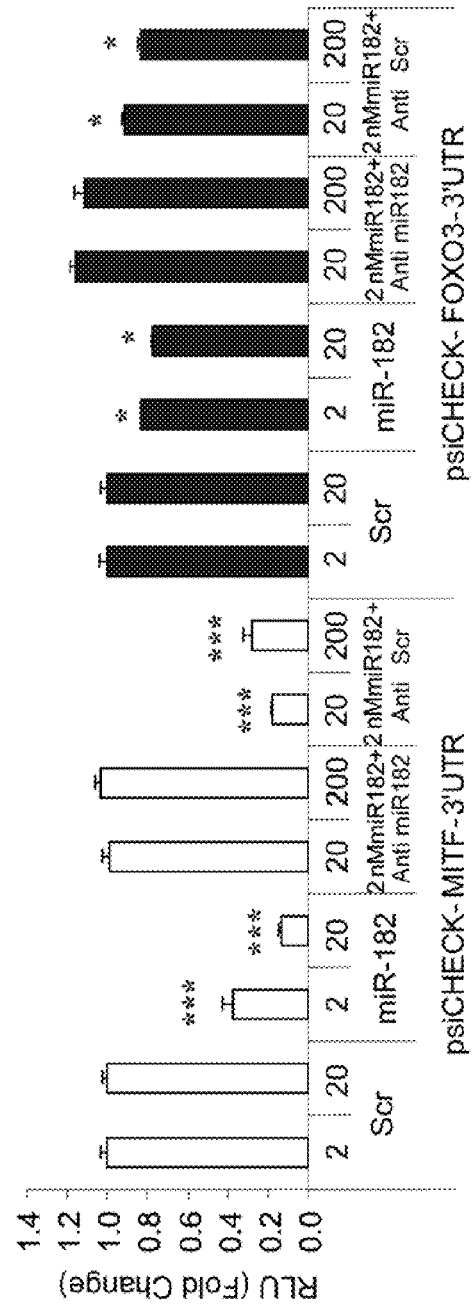
Figure 4D:
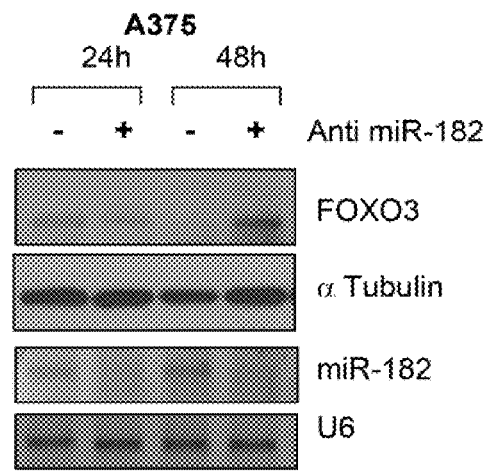

In order to determine whether FOXO3 and CASP2 are direct targets of miR-182, fragments of the FOXO3 3'-untranslated region (3'-UTR) and CASP2-3'UTR containing the miR-182 binding sites (REs) were sub-cloned into the psiCHECK2 dual luciferase vector (FIG. 4B). A 1 Kb portion of MITF-M 3'UTR containing three binding sites was used as a positive control. These reporter vectors were then co-transfected with miRIDIAN hsa-mir-182 mimic oligonucleotides or microRNA mimic negative control. A consistent and dose-dependent reduction of luciferase activity was observed upon miR-182 transfection in different cell lines, particularly in those carrying low endogenous levels (FIG. 4B). Moreover, co-transfection with the complementary oligonucleotides (miRIDIAN hsa-mir-182 inhibitor oligonucleotide) restored luciferase levels (FIG. 4C). Further evidence that endogenous miR-182 actively blocks Foxo3 and MITF in melanoma cells came from the observation that transfection of anti-miR-182 oligonucleotides results in Foxo3 and MITF up-regulation (FIG. 4D). Moroever, Foxo3 induction led to Bim activation, further emphasizing the functional impact of miR-182 on the FOXO3 pathway.

Figure 4E:
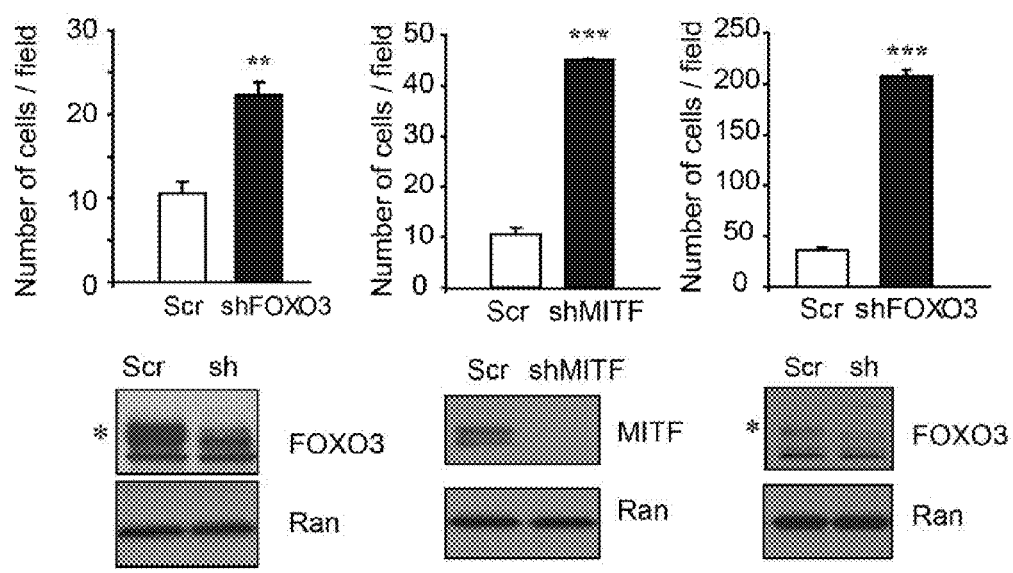
Figure 4F:
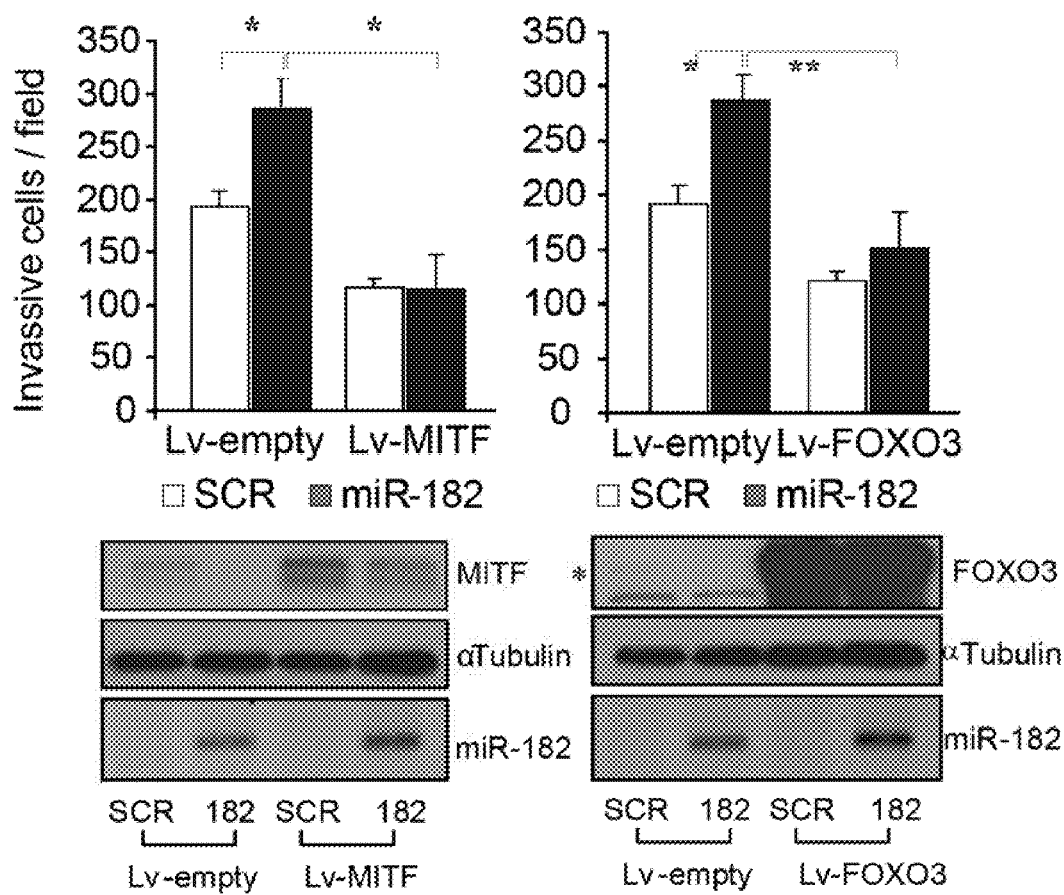

To determine whether Foxo3 and MITF are critical mediators of miR-182's role in melanoma metastasis, they were downregulated using RNAi in melanoma cell lines. Foxo3 RNAi enhanced the invasive potential of melanoma cell lines (P=0.004) to a degree comparable to that caused by miR-182 overexpression (FIG. 4E). Similarly, abolition of MITF expression promoted the migratory behavior of melanoma cells to an extent similar to that seen with miR-182 overexpression (approximately 5-fold; P=0.0001) (FIG. 4E). Finally, concomitant overexpression of miR-182 and either Foxo3 or MITF-M abolished the stimulatory effect of miR-182 on the invasive capacity of melanoma cells (FIG. 4F), demonstrating that Foxo3 and MITF repression are necessary effectors of miR-182.

Example 8 miRNA Targeting Against Human Melanoma

To assess the effect of downregulating in vitro miR-182 (SEQ ID NO: 1), miR-183 (SEQ ID NO: 8), miR-96 (SEQ ID NO:5), miR-335 (SEQ ID NO:6) or combinations thereof in human melanocytes and melanoma cell lines (primary and metastatic), specific oligonucleotide antisense or lentiviral vectors expressing a tetracycline-inducible short-hairpin are introduced into different melanoma cell lines. Suitable cell lines include those that are related to the cell type to which delivery of a modified oligonucleotide is desired in vivo. For example, suitable cell lines for the study of modified oligonucleotides for the treatment of melanoma cancer include cell lines such as: primary cultures of normal human neonatal and adult melanocytes (Lonza), human immortalized melanocytes (Hermes), human primary melanoma cell lines including nodular (WM278, WM39) or superficial spreading melanoma (WM35, WM1552C), human metastatic melanoma cell lines (SK-MEL-19, -29, -85, -94, -100, -103, -147, -173, -187, -192, -197), A375 (ATCC) and 501MEL, mouse immortalized melanocytes ('melan-a') and mouse metastatic melanoma cells (B16F 10).

Suitable Anti-miRNA Strategies May Include:

oligonucleotide antisense (miRIDIAN microRNA inhibitors, Dharmacon) which are single-stranded chemically enhanced oligonucleotides designed to inhibit the endogenous miRNAs, delivered to cells as part of liposomal complexes (Lipofectamine 2000, Invitrogen). Fluorescently labeled scrambled oligonucleotides are used as controls of the efficiency of transfection (BLOCK-IT Invitrogen). Alternatively, oligonucleotides generated by other companies (e.g., Regulus, Exiqon) and chemically-modified for an improved in vivo delivery, will be tested in vitro.

Lentiviral vectors expressing a tetracycline-inducible short-hairpin and red fluorescent reporter gene (LTR-TET-RFP-shRNA).

To assess the proliferation/viability of the transfected/infected cells several assays are used:

Growth curves. Cells are seeded, treated with the corresponding antimiRNA antisense or vectors (4n per condition). At indicated times; cells are fixed with 1% glutaraldehyde and stained with crystal violet. After extensive washing, crystal violet is resolubilized in 15% acetic acid and absorbance is measured at 595 nm.

Trypan blue exclusion assay.

WST-1 proliferation assays.

Apoptosis assays. Annexin-V/Propidium Iodide staining, TUNEL assay, both quantitated by flow cytometry (FACS).

Chemosensitivity assays. Viability and apoptosis assays will be repeated combining cytotoxic drugs (cisplatinum, taxol) and antimiRNA antisense/lenti-shRNA vectors.

To determine the impact of miRNA downregulation on the ability of the cells to migrate (a property of metastatic cells) several migration assays are used:

Wound-healing assays. An artificial "wound" is created using a 10 µl pipette tip on confluent cell monolayer in 4-chambers plates (Lab-Tek II chambered 1.5 coverglass system 155382 Nalge Nunc International) in complete medium. Photographs are taken every 10 minutes during 12 hours using a Confocal Ultra-Spectral microscope Leica.

Cell Adhesion Assay. 24-well culture plates are coated with native triple helical or thermally denatured collagen types I and IV (10.0 µg/ml) for 12 hours at 4° C. The plates are washed with PBS and nonspecific binding sites blocked by incubation with 1.0% bovine serum albumin (BSA) in PBS for 1 hour at 37° C. Tumor cells (transduced with scrambled or antimiRNAs) from subconfluent cultures are harvested, washed, and resuspended in adhesion buffer containing RPMI 1640, 1 mmol/L $MgCl_2$, 0.2 mmol/L $MnCl_2$, and 0.5% BSA. Tumor cells are added to the coated plates in a total volume of 200 µl and allowed to attach for 15 to 30 minutes. Nonattached cells are removed by washing and attached cells are stained with crystal violet. Cell adhesion are quantified by measuring the optical density of eluted crystal violet from attached cells at a wavelength of 600 nm.

Cell Migration Assay. Membranes (8.0-µm pore size) from transwell migration chambers are coated with native triple helical or thermally denatured collagen type I or IV (10.0 µg/ml) for 12 hours at 4° C. The transwells are next washed with PBS and nonspecific binding sites blocked by incubation with 1.0% BSA in PBS for 1 hour at 37° C. Tumor cells (control or antimiRNA treated) from subconfluent cultures are harvested, washed, and resuspended in migration buffer containing RPMI 1640, 1 mmol/L $MgCl_2$, 0.2 mmol/L $MnCl_2$, and 0.5% BSA. Tumor cells are allowed to migrate to the underside of the coated transwell membranes for 2 to 4 hours. Tumor cells remaining on the top-side of the membrane are removed and cells that had migrated to the underside are stained with crystal violet as described previously. Cell migration is quantified by direct cell counts per microscopic field.

To verify the ability to target specific miRNAs by confirming the upregulation at the protein level of some of the predicted or validated miRNA targets, Western blots analysis are preformed.

Example 9

Determination of the Anti-Tumor Potential of Targeting miR-182 (SEQ ID NO: 1), miR-183 (SEQ ID NO: 8), miR-96 (SEQ ID NO: 5) or miR-335 (SEQ ID NO: 6) in in vivo Melanoma Models Primary human melanoma xenograft, while growing locally, is able to invade, spread, and originate distant (lung) metastases after surgical resection of the primary lesion. This process mimics the usual clinical behavior of malignant melanoma. Therefore, this model might represent an ideal pre-clinical setting in which testing the anti-tumoral action of systemic anti-miRNA delivery against different phases of tumor progression (primary growth, invasion, metastasis).

Initial experiments are performed to determine the adequate number of human melanoma cells to be injected subcutaneously to allow formation of a primary tumor, initial local invasion and tumor spread in 4-6 weeks. A375 cells ($1 \times 10^6$ cells, $2 \times 10^6$, $4 \times 10^6$; n=5 animals per group) stably transduced with a lentiviral vector carrying the Luciferase cDNA (Fuw-Luc) are combined with matrigel and injected sub-cutaneously into the flanks of athymic nude mice. Animals are examined daily and tumors measured twice weekly with caliper. The primary tumor mass is surgically removed after 4 weeks (or once it reaches a 1 cm³ volume), and the animals kept alive for additional 6 weeks and regularly monitored for luciferase expression (IVIS, Xenogen). At this point, mice are sacrificed, their lungs are perfused with 4% paraformaldehyde (PFA) and the number of macroscopic metastases is counted. The minimal amount of cells that allows the appearance of distant metastases in less than 6 weeks post-removal of the primary tumor is selected for preclinical studies.

Mice: 15 athymicnude male mice (6-8 weeks old), distributed as indicated in Table II.

total duration of 8 weeks), starting 2 weeks after tumor induction. Test & Control antimiRNAs (oligonucleotides or shRNA-lentiviruses) are intravenously (IV) injected directly into one of the tail veins as bolus injections, using a suitable needle. In case the IV route is not feasible (for any reason) during the treatment period, the respective material is to be injected intraperitoneally (IP). In all instances, dosing solutions are applied as a single injection on each of the repeated dosing sessions. The dose level, volume dosage and/or dose volume are to be determined prior to the treatment phase.

Mice: 60 male mice (6-8 weeks old), distributed as indicated in Table III.

TABLE III

| | | INDUCTION | | | TREATMENT | | | | |
|---|---|---|---|---|---|---|---|---|---|
| Group # | Group Size | Tumor cells | Route | #cells | Test material | Route | Dose | Freq & Duration | Scheduled termination |
| 1 | n = 10 | A375-Luc | SC | To be determined | oligo | IV/IP | To be determined | 3×week, for 8 weeks | 70 days |
| 2 | n = 10 | | | | vehicle oligo | | | | |
| 3 | n = 10 | | | | | | | | |
| 4 | n = 10 | | | | vehicle | | | | |
| 5 | n = 10 | | | | Lenti-shRNA | | | | |
| 6 | n = 10 | | | | Lenti-Ø | | | | |

TABLE II

| Group # | Group size | Tumor cells | Route | Dose cells (# cells/0.1 ml) | Scheduled Surgery | Scheduled Termination post-Induction |
|---|---|---|---|---|---|---|
| 1 | n = 5 | A375-Luc | SC | 1 × 10⁶ cells | 28 days | 70 days |
| 2 | n = 5 | | | 2 × 10⁶ cells | | |
| 3 | n = 5 | | | 4 × 10⁶ cells | | |

Luciferase imaging: tumor dissemination and metastasis formation are monitored by in vivo luciferase imaging. Mice are anesthetized by isoflurane inhalation and injected with D-luciferin (Xenogen) at 50 mg/Kg intraperitoneally. Photonic emission is imaged using the In Vivo Imaging System (IVIS, Xenogen). Tumor bioluminescence is quantified by integrating the photonic flux (photons per second) through a circular region encircling each tumor as determined by the LIVING IMAGES software package (Xenogen). Statistical significance of differences in tumor size between groups is estimated using a t-test.

Resection of lungs: Mice are sacrificed; lungs are perfused with 4% PFA, removed and photographed with a digital camera adapted to a dissecting scope (Leika). The total number of isolated and discrete lung superficial lesions (macrometastases) is carefully quantitated in each lobe for each specimen. Number of metastases is represented as a mean of superficial melanoma lesions per lung and per experimental condition.

To determine the most efficient anti-miRNA method (oligonucleotide vs lentivirus) dose and administration route (IV/IP) that produces a more significant anti-tumor effect with the lowest associated toxicity, each animal in this step of the study is subjected to a total of 24 repeated injections (3 dosing sessions/week, interspaced by at least 1-day intervals, for a Collection of Blood Samples: Final blood samples, individually collected into noncoated tubes prior to the respective scheduled termination, are obtained by retroorbital sinus bleeding under light CO2 anesthesia from all the animals assigned to Aims 2.2 and 2.3. All serum samples are kept frozen [(−70)-(−80)° C.] for further analyses.

Organ/Tissue Collection, Weighing & Fixations. At the respective scheduled surgery, the primary tumor mass are excised and weighed, if applicable. In addition, at termination, spleen, kidney, brain, liver & lungs are collected from all the animals and cut into 2 portions: one portion is fixed in 10% neutral buffered formalin while the other portion is be frozen and stored in liquid nitrogen.

Histological analyses. Formalin-fixed, paraffin embedded samples (representative of all tissues collected) are sectioned (5 μm) and conventional hematoxylin/eosin (H&E) staining is performed for overall histopathological evaluation. AntimiR effects on cell proliferation and apoptosis are determined by Ki67 (NCL-Ki67p, Novocastra, Vector labs) and "activated caspase-3" immunostaining on sections of the primary tumor. Presence of micrometastases in distal organs is determined by immunohistochemistry with melanoma markers (e.g. S100, SOX10, melan-a, Tyrosinase). Our automated IHC method (Ventana) follows a conventional avidin-biotin immunoperoxidase technique, with small variations on the antigen retrieval method for certain epitopes, diaminobenzidine as chromogen and hematoxylin for nuclear counterstaining.

Biomarker (endpoint) analyses: Total RNA from primary and metastatic melanoma tissue is extracted using the mirVana microRNA extraction kit (Ambion, Ltd.). Quantitative real-time PCR (qRT-PCR) analysis of the corresponding miRNAs is performed by using the miRNA-specific mirVana qRT-PCR Primer set (Ambion). First, 200 ng of total RNA is reversed transcribed by using the corresponding mirVana RT Primer and the mirVana microRNA Detection kit (Ambion) at +37° C. for 30 min, followed by enzyme inactivation at +95°

C. for 10 min. Then, PCR is performed by adding the mirVana PCR primers and the SYBR Green master mix (Ambion). Both melting curve analysis and agarose gel run are conducted to confirm the specificity of the amplification reactions. For normalization, expression of the U6 small RNA will be measured for each RNA sample.

To indirectly confirm the downregulation of the corresponding miRNAs, the expression of some of their validated targets are analyzed by immunohistochemistry and Western blot in tumor samples extracted from treated animals and compared with control (untreated) tumors.

REFERENCES

Bandres, E., Cubedo, E., Agirre, X., Malumbres, R., Zarate, R., Ramirez, N., Abajo, A., Navarro, A., Moreno, I., Monzo, M., and Garcia-Foncillas, J. (2006). Identification by Real-time PCR of 13 mature microRNAs differentially expressed in colorectal cancer and non-tumoral tissues. Mol Cancer 5, 29.

Bastian, B. C., LeBoit, P. E., Hamm, H., Brocker, E. B., and Pinkel, D. (1998). Chromosomal gains and losses in primary cutaneous melanomas detected by comparative genomic hybridization. Cancer Res 58, 2170-2175.

Benjamin, C. L., Melnikova, V. O., and Ananthaswamy, H. N. (2007). Models and mechanisms in malignant melanoma. Mol Carcinog 46, 671-678.

Calin, G. A., and Croce, C. M. (2006). MicroRNA signatures in human cancers. Nat Rev Cancer 6, 857-866.

Calin, G. A., Ferracin, M., Cimmino, A., Di Leva, G., Shimizu, M., Wojcik, S. E., Iorio, M. V., Visone, R., Sever, N. I., Fabbri, M., et al. (2005). A MicroRNA signature associated with prognosis and progression in chronic lymphocytic leukemia. N Engl J Med 353, 1793-1801.

Chen, C. Z., Li, L., Lodish, H. F., and Bartel, D. P. (2004). MicroRNAs modulate hematopoietic lineage differentiation. Science 303, 83-86.

Chin, L., Garraway, L. A., and Fisher, D. E. (2006). Malignant melanoma: genetics and therapeutics in the genomic era. Genes Dev 20, 2149-2182.

Cimmino, A., Calin, G. A., Fabbri, M., Iorio, M. V., Ferracin, M., Shimizu, M., Wojcik, S. E., Aqeilan, R. I., Zupo, S., Dono, M., et al. (2005). miR-15 and miR-16 induce apoptosis by targeting BCL2. Proc Natl Acad Sci USA 102, 13944-13949.

Croce, C. M., and Calin, G. A. (2005). miRNAs, cancer, and stem cell division. Cell 122, 6-7.

Cullen, B. R. (1987). Use of eukaryotic expression technology in the functional analysis of cloned genes. Methods Enzymol 152, 684-704.

Dickins, R. A., Hemann, M. T., Zilfou, J. T., Simpson, D. R., Ibarra, I., Hannon, G. J., and Lowe, S. W. (2005). Probing tumor phenotypes using stable and regulated synthetic microRNA precursors. Nat Genet. 37, 1289-1295.

Garraway, L. A., Widlund, H. R., Rubin, M. A., Getz, G., Berger, A. J., Ramaswamy, S., Beroukhim, R., Milner, D. A., Granter, S. R., Du, J., et al. (2005). Integrative genomic analyses identify MITF as a lineage survival oncogene amplified in malignant melanoma. Nature 436, 117-122.

Gaur, A., Jewell, D. A., Liang, Y., Ridzon, D., Moore, J. H., Chen, C., Ambros, V. R., and Israel, M. A. (2007). Characterization of microRNA expression levels and their biological correlates in human cancer cell lines. Cancer Res 67, 2456-2468.

Geller, A. C., Swetter, S. M., Brooks, K., Demierre, M. F., and Yaroch, A. L. (2007). Screening, early detection, and trends for melanoma: current status (2000-2006) and future directions. J Am Acad Dermatol 57, 555-572; quiz 573-556.

Gray-Schopfer, V. C., Cheong, S. C., Chong, H., Chow, J., Moss, T., Abdel-Malek, Z. A., Marais, R., Wynford-Thomas, D., and Bennett, D. C. (2006). Cellular senescence in naevi and immortalisation in melanoma: a role for p16? Br J Cancer 95, 496-505.

Guo, Y., Chen, Z., Zhang, L., Zhou, F., Shi, S., Feng, X., Li, B., Meng, X., Ma, X., Luo, M., et al. (2008). Distinctive microRNA profiles relating to patient survival in esophageal squamous cell carcinoma. Cancer Res 68, 26-33.

Gutgemann, A., Golob, M., Muller, S., Buettner, R., and Bosserhoff, A. K. (2001). Isolation of invasion-associated cDNAs in melanoma. Arch Dermatol Res 293, 283-290.

Hayashita, Y., Osada, H., Tatematsu, Y., Yamada, H., Yanagisawa, K., Tomida, S., Yatabe, Y., Kawahara, K., Sekido, Y., and Takahashi, T. (2005). A polycistronic microRNA cluster, miR-17-92, is overexpressed in human lung cancers and enhances cell proliferation. Cancer Res 65, 9628-9632.

He, L., and Hannon, G. J. (2004). MicroRNAs: small RNAs with a big role in gene regulation. Nat Rev Genet. 5, 522-531.

He, L., Thomson, J. M., Hemann, M. T., Hemando-Monge, E., Mu, D., Goodson, S., Powers, S., Cordon-Cardo, C., Lowe, S. W., Hannon, G. J., and Hammond, S. M. (2005). A microRNA polycistron as a potential human oncogene. Nature 435, 828-833.

Hebert, C., Norris, K., Scheper, M. A., Nikitakis, N., and Sauk, J. J. (2007). High mobility group A2 is a target for miRNA-98 in head and neck squamous cell carcinoma. Mol Cancer 6, 5.

Hernando, E., Nahle, Z., Juan, G., Diaz-Rodriguez, E., Alaminos, M., Hemann, M., Michel, L., Mittal, V., Gerald, W., Benezra, R., et al. (2004). Rb inactivation promotes genomic instability by uncoupling cell cycle progression from mitotic control. Nature 430, 797-802.

Jansen, B., Wacheck, V., Heere-Ress, E., Schlagbauer-Wadl, H., Hoeller, C., Lucas, T., Hoermann, M., Hollenstein, U., Wolff, K., and Pehamberger, H. (2000). Chemosensitisation of malignant melanoma by BCL2 antisense therapy. Lancet 356, 1728-1733.

Johnson, S. M., Grosshans, H., Shingara, J., Byrom, M., Jarvis, R., Cheng, A., Labourier, E., Reinert, K. L., Brown, D., and Slack, F. J. (2005). RAS is regulated by the let-7 microRNA family. Cell 120, 635-647.

Jonsson, G., Dahl, C., Staaf, J., Sandberg, T., Bendahl, P. O., Ringner, M., Guldberg, P., and Borg, A. (2007). Genomic profiling of malignant melanoma using tiling-resolution arrayCGH. Oncogene.

Landgraf, P., Rusu, M., Sheridan, R., Sewer, A., Iovino, N., Aravin, A., Pfeffer, S., Rice, A., Kamphorst, A. O., Landthaler, M., et al. (2007). A mammalian microRNA expression atlas based on small RNA library sequencing. Cell 129, 1401-1414.

Lee, Y. S., and Dutta, A. (2007). The tumor suppressor microRNA let-7 represses the HMGA2 oncogene. Genes Dev 21, 1025-1030.

Levy, C., Khaled, M., and Fisher, D. E. (2006). MITF: master regulator of melanocyte development and melanoma oncogene. Trends Mol Med 12, 406-414.

Lim, L. P., Lau, N. C., Garrett-Engele, P., Grimson, A., Schelter, J. M., Castle, J., Bartel, D. P., Linsley, P. S., and Johnson, J. M. (2005). Microarray analysis shows that some microRNAs downregulate large numbers of target mRNAs. Nature 433, 769-773.

Loercher, A. E., Tank, E. M., Delston, R. B., and Harbour, J. W. (2005). MITF links differentiation with cell cycle arrest in melanocytes by transcriptional activation of INK4A. J Cell Biol 168, 35-40.

Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.

Ma, L., Teruya-Feldstein, J., and Weinberg, R. A. (2007). Tumour invasion and metastasis initiated by microRNA-10b in breast cancer. Nature 449, 682-688.

Mayr, C., Hemann, M. T., and Bartel, D. P. (2007). Disrupting the pairing between let-7 and Hmga2 enhances oncogenic transformation. Science 315, 1576-1579.

Meister, G., Landthaler, M., Dorsett, Y., and Tuschl, T. (2004). Sequence-specific inhibition of microRNA- and siRNA-induced RNA silencing. Rna 10, 544-550.

Myatt, S. S., and Lam, E. W. (2007). The emerging roles of forkhead box (Fox) proteins in cancer. Nat Rev Cancer 7, 847-859.

Natali, P. G., Nicotra, M. R., Di Renzo, M. F., Prat, M., Bigotti, A., Cavaliere, R., and Comoglio, P. M. (1993). Expression of the c-Met/HGF receptor in human melanocytic neoplasms: demonstration of the relationship to malignant melanoma tumour progression. Br J Cancer 68, 746-750.

Nguyen, D. X., and Massague, J. (2007). Genetic determinants of cancer metastasis. Nat Rev Genet. 8, 341-352.

Ovcharenko, D., Kelnar, K., Johnson, C., Leng, N., and Brown, D. (2007). Genome-scale microRNA and small interfering RNA screens identify small RNA modulators of TRAIL-induced apoptosis pathway. Cancer Res 67, 10782-10788.

Paik, J. H., Kollipara, R., Chu, G., Ji, H., Xiao, Y., Ding, Z., Miao, L., Tothova, Z., Horner, J. W., Carrasco, D. R., et al. (2007). FoxOs are lineage-restricted redundant tumor suppressors and regulate endothelial cell homeostasis. Cell 128, 309-323.

Poser, I., and Bosserhoff, A. K. (2004). Transcription factors involved in development and progression of malignant melanoma. Histol Histopathol 19, 173-188.

Reed, J. A., and Medrano, E. E. (2006). Recent advances in melanoma research. Front Biosci 11, 3003-3013.

Salti, G. I., Manougian, T., Farolan, M., Shilkaitis, A., Majumdar, D., and Das Gupta, T. K. (2000). Micropthahnia transcription factor: a new prognostic marker in intermediate-thickness cutaneous malignant melanoma. Cancer Res 60, 5012-5016.

Selzer, E., Wacheck, V., Lucas, T., Heere-Ress, E., Wu, M., Weilbaecher, K. N., Schlegel, W., Valent, P., Wrba, F., Pehamberger, H., et al. (2002). The melanocyte-specific isoform of the microphthalmia transcription factor affects the phenotype of human melanoma. Cancer Res 62, 2098-2103.

Smalley, K. S., and Herlyn, M. (2005). Targeting intracellular signaling pathways as a novel strategy in melanoma therapeutics. Ann N Y Acad Sci 1059, 16-25.

Takamizawa, J., Konishi, H., Yanagisawa, K., Tomida, S., Osada, H., Endoh, H., Harano, T., Yatabe, Y., Nagino, M., Nimura, Y., et al. (2004). Reduced expression of the let-7 microRNAs in human lung cancers in association with shortened postoperative survival. Cancer Res 64, 3753-3756.

Tanami, H., Imoto, I., Hirasawa, A., Yuki, Y., Sonoda, I., Inoue, J., Yasui, K., Misawa-Furihata, A., Kawakami, Y., and Inazawa, J. (2004). Involvement of overexpressed wild-type BRAF in the growth of malignant melanoma cell lines. Oncogene 23, 8796-8804.

Tavazoie, S. F., Alarcon, C., Oskarsson, T., Padua, D., Wang, Q., Bos, P. D., Gerald, W. L., and Massague, J. (2008). Endogenous human microRNAs that suppress breast cancer metastasis. Nature 451, 147-152.

Thomson, J. M., Newman, M., Parker, J. S., Morin-Kensicki, E. M., Wright, T., and Hammond, S. M. (2006). Extensive post-transcriptional regulation of microRNAs and its implications for cancer. Genes Dev 20, 2202-2207.

Trent, J. M., Meyskens, F. L., Salmon, S. E., Ryschon, K., Leong, S. P., Davis, J. R., and McGee, D. L. (1990). Relation of cytogenetic abnormalities and clinical outcome in metastatic melanoma. N Engl J Med 322, 1508-1511.

Voorhoeve, P. M., le Sage, C., Schrier, M., Gillis, A. J., Stoop, H., Nagel, R., Liu, Y. P., van Duijse, J., Drost, J., Griekspoor, A., et al. (2006). A genetic screen implicates miRNA-372 and miRNA-373 as oncogenes in testicular germ cell tumors. Cell 124, 1169-1181.

Willmore-Payne, C., Holden, J. A., Hirschowitz, S., and Layfield, L. J. (2006). BRAF and c-kit gene copy number in mutation-positive malignant melanoma. Hum Pathol 37, 520-527.

Xu, S., Witmer, P. D., Lumayag, S., Kovacs, B., and Valle, D. (2007). MicroRNA (miRNA) transcriptome of mouse retina and identification of a sensory organ-specific miRNA cluster. J Biol Chem 282, 25053-25066.

Yanaihara, N., Caplen, N., Bowman, E., Seike, M., Kumamoto, K., Yi, M., Stephens, R. M., Okamoto, A., Yokota, J., Tanaka, T., et al. (2006). Unique microRNA molecular profiles in lung cancer diagnosis and prognosis. Cancer Cell 9, 189-198.

Yi, R., O'Carroll, D., Pasolli, H. A., Zhang, Z., Dietrich, F. S., Tarakhovsky, A., and Fuchs, E. (2006). Morphogenesis in skin is governed by discrete sets of differentially expressed microRNAs. Nat Genet. 38, 356-362.

Yu, S. L., Chen, H. Y., Chang, G. C., Chen, C. Y., Chen, H. W., Singh, S., Cheng, C. L., Yu, C. J., Lee, Y. C., Chen, H. S., et al. (2008). MicroRNA Signature Predicts Survival and Relapse in Lung Cancer. Cancer Cell 13, 48-57.

Zhang, L., Huang, J., Yang, N., Greshock, J., Megraw, M. S., Giannakakis, A., Liang, S., Naylor, T. L., Barchetti, A., Ward, M. R., et al. (2006). microRNAs exhibit high frequency genomic alterations in human cancer. Proc Natl Acad Sci USA 103, 9136-9141.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for treating melanoma comprising administering to a subject having melanoma an effective amount of a composition comprising an isolated nucleic acid comprising a nucleic acid sequence that is complementary to SEQ ID NO: 1, or to a sequence at least about 80% identical thereto.

2. The method of claim 1, wherein the nucleic acid is a modified oligonucleotide.

3. The method of claim 1, wherein the nucleic acid is a vector comprising said nucleic acid sequence.

4. The method of claim 1, wherein the subject is a human.

5. The method of claim 2, wherein the nucleic acid sequence of the modified oligonucleotide has no more than two mismatches to SEQ ID NO: 1.

6. The method of claim 2, wherein the nucleic acid sequence of the modified oligonucleotide has no more than one mismatch to SEQ ID NO: 1.

7. The method of claim 1, wherein the administration comprises intravenous administration, intraperitoneal administration, subcutaneous administration, intratumoral administration, or chemoembolization.

8. The method of claim 1, wherein the composition is administered in combination with at least one other anticancer agent in unit dosage form.

9. The method of claim 8, wherein the anticancer agent is selected from the group consisting of dacarbazine (DTIC), hydroxylurea, temozolomide, cisplatin, carboplatin, camptothecins, doxorubicin, cyclophosphamide, etoposide, vinblastine, Actinomycin D and cloposide.

10. A method for increasing an expression of forkhead box O3 transcription factor (FOXO3) in a melanoma cell, the method comprising introducing to said cell an effective amount of a nucleic acid comprising a nucleic acid sequence that is complementary to SEQ ID NO: 1 or sequences at least about 80% identical thereto, wherein said nucleic acid increases the expression of FOXO3.

* * * * *

SEQUENCE LISTING

<160> NUMBER OF SEQ ID NOS: 21

<210> SEQ ID NO 1
<211> LENGTH: 24
<212> TYPE: RNA
<213> ORGANISM: Homo sapiens

<400> SEQUENCE: 1
uuuggcaaug guagaacuca cacu                                              24

<210> SEQ ID NO 2
<211> LENGTH: 22
<212> TYPE: RNA
<213> ORGANISM: Homo sapiens

<400> SEQUENCE: 2
uagcaccauc ugaaaucggu ua                                                22

<210> SEQ ID NO 3
<211> LENGTH: 22
<212> TYPE: RNA
<213> ORGANISM: Homo sapiens

<400> SEQUENCE: 3
aacccguaga uccgaacuug ug                                                22

<210> SEQ ID NO 4
<211> LENGTH: 23
<212> TYPE: RNA
<213> ORGANISM: Homo sapiens

<400> SEQUENCE: 4
cccaguguuu agacuaucug uuc                                               23

<210> SEQ ID NO 5
<211> LENGTH: 23
<212> TYPE: RNA
<213> ORGANISM: Homo sapiens

<400> SEQUENCE: 5
uuuggcacua gcacauuuuu gcu                                               23

<210> SEQ ID NO 6
<211> LENGTH: 23
<212> TYPE: RNA
<213> ORGANISM: Homo sapiens

<400> SEQUENCE: 6
ucaagagcaa uaacgaaaaa ugu                                               23

<210> SEQ ID NO 7
<211> LENGTH: 110
<212> TYPE: RNA
<213> ORGANISM: Homo sapiens

<400> SEQUENCE: 7
gagcugcuug ccuccccccg uuuuuggcaa ugguagaacu cacacuggug agguaacagg       60
auccggugcu ucuagacuug ccaacuaugg ggcgaggacu cagccggcac                 110

<210> SEQ ID NO 8
<211> LENGTH: 22
<212> TYPE: RNA

<213> ORGANISM: Homo sapiens

<400> SEQUENCE: 8
uauggcacug guagaauuca cu                                              22

<210> SEQ ID NO 9
<211> LENGTH: 64
<212> TYPE: RNA
<213> ORGANISM: Homo sapiens

<400> SEQUENCE: 9
augacugauu ucuuugggug uucagaguca auauaauuuu cuagcaccau cugaaaucgg      60
uuau                                                                  64

<210> SEQ ID NO 10
<211> LENGTH: 80
<212> TYPE: RNA
<213> ORGANISM: Homo sapiens

<400> SEQUENCE: 10
ccuguugcca caaacccgua gauccgaacu uguggvauua guccgcacaa gcuuguaucu      60
auagguaugu gucuguuagg                                                  80

<210> SEQ ID NO 11
<211> LENGTH: 110
<212> TYPE: RNA
<213> ORGANISM: Homo sapiens

<400> SEQUENCE: 11
ccagaggaca ccuccacucc gucuacccag uguuuagacu aucguucag gacucccaaa      60 uuguacagua gucugcacau ugguuaggcu gggcuggguu agacccucgg                110

<210> SEQ ID NO 12
<211> LENGTH: 78
<212> TYPE: RNA
<213> ORGANISM: Homo sapiens

<400> SEQUENCE: 12
uggccgauuu uggcacuagc acauuuuugc uugugucucu ccgcucugag caaucaugug      60
cagugccaau augggaaa                                                    78

<210> SEQ ID NO 13
<211> LENGTH: 94
<212> TYPE: RNA
<213> ORGANISM: Homo sapiens

<400> SEQUENCE: 13 uguuugagc gggggucaag agcaauaacg aaaaauguuu gucauaaacc guuuucauu       60 auugcuccug accuccucuc auuugcuaua uuca                                  94

<210> SEQ ID NO 14
<211> LENGTH: 110
<212> TYPE: RNA
<213> ORGANISM: Homo sapiens

<400> SEQUENCE: 14
ccgcagagug ugacuccugu ucuguguaug gcacugguag aauucacugu gaacagucuc      60
agucagugaa uuaccgaagg gccauaaaca gagcagagac agauccacga                110

<210> SEQ ID NO 15

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgccctaggg atggtgtct                                                    19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccctcactcc tcgattcaga                                                   20

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagaagggtt aacaaggcct ccccagctcc tgg                                    33

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcctcgagc ctcgctggct gtgcaca                                           27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcgagtcac tgaggaaggg gaagtg                                            26

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggccgctg tgctaatcag agcatcgtt                                         29

<210> SEQ ID NO 21
<211> LENGTH: 975
<212> TYPE: DNA
```

```
<213> ORGANISM: Homo sapiens

<400> SEQUENCE: 21
aggatcactg aggaagggga agtgggcaaa gcagaccctc aaactgacac aagacctaca        60
gagaaaaccc tttgccaaat ctgctctcag caagtggaca gtgataccgt ttacagctta       120
acacctttgt gaatcccacg ccattttcct aacccagcag agactgttaa tggcccctta       180
ccctgggtga agcacttacc cttggaacag aactctaaaa agtatgcaaa atcttccttg       240
tacagggtgg tgagccgcct gccagtggag gacagcaccc ctcagcacca cccaccctca       300
ttcagagcac accgtgagcc cccgtcggcc attctgtggt gttttaatat tgcgatggtt       360
tatgggacgt tttaagtgtt gttcttgtgt ttgttttcct ttgactttct gagtttttca       420
catgcattaa cttgcggtat ttttctgtta aaatgttaac cgtccttccc ctagcaaatt       480
taaaaacaga aagaaaatgt tgtaccagtt accattccgg gttcgagcat cacaagcttt       540
tgagcgcatg gaactccata aactaacaaa ttacataaac taaaggggga ttttctttct       600
tcttttgttt ggtagaaaat tatccttttc taaaaactga acaatggcac aattgtttgc       660
tatgtgcacc cgtccaggac agaaccgtgc ataggcaaaa ggagtggagc acagcgtccg       720
gcccagtgtg tttccggttc tgagtcaggg tgatctgtgg acgggacccc agcaccaagt       780
ctacgggtgc cagatcagta gggcctgtga tttcctgtca gtgtcctcag ctaatgtgaa       840
cagtgttggt ctgctggtta gaaactagaa tattgatatt ttcaggaaag aaatcagctc       900
agctctccac tcattgccaa atgtcactaa agggtttagt tttaaggaga aagaaaagga       960
aaaaaaaaaa aaaca                                                        975
```